(12) United States Patent
Hu et al.

(10) Patent No.: US 8,304,394 B2
(45) Date of Patent: Nov. 6, 2012

(54) LOW SIDE EFFECT PHARMACEUTICAL COMPOSITION CONTAINING ISONIAZID

(75) Inventors: Yoapu Oliver Hu, Taipei (TW); Ton ho Young, Sindian (TW)

(73) Assignee: National Defense Education and Research Foundation, Taipei (TW)

( * ) Notice: Subject to any disclaimer, the term of this patent is extended or adjusted under 35 U.S.C. 154(b) by 124 days.

(21) Appl. No.: 13/059,929

(22) PCT Filed: Jul. 23, 2008

(86) PCT No.: PCT/CN2008/001353
§ 371 (c)(1),
(2), (4) Date: Feb. 18, 2011

(87) PCT Pub. No.: WO2010/009572
PCT Pub. Date: Jan. 28, 2010

(65) Prior Publication Data
US 2011/0207684 A1 Aug. 25, 2011

(51) Int. Cl.
*A61K 31/7048* (2006.01)
*A61K 31/4409* (2006.01)
*A61K 31/661* (2006.01)
*A61K 31/06* (2006.01)

(52) U.S. Cl. ............. 514/23; 514/27; 514/133; 514/354

(58) Field of Classification Search ............ 514/23, 514/27, 133, 354
See application file for complete search history.

(56) References Cited

U.S. PATENT DOCUMENTS 5,585,243 A * 12/1996 Aster et al. .................. 435/7.21
6,500,868 B2 * 12/2002 Bobotas ........................ 514/654
6,514,541 B2 * 2/2003 Khanuja et al. ............... 424/747

* cited by examiner

*Primary Examiner* — Raymond Henley, III
(74) *Attorney, Agent, or Firm* — Muncy, Geissler, Olds & Lowe, PLLC

(57) ABSTRACT

The present invention features a novel, low side-effect pharmaceutical compound complex, comprising the pharmaceutically effective dose of isoniazid (INH) and pharmaceutically effective dose of one of the following compounds. Said compound was selected from the following groups of compounds: Nordihydroguaiaretic acid, Trans-Cinnamaldehyde, Daidzein, Isovitexin, Kaempferol, disulfuram, β-Myrcene, Quercetin, (−)-Epigallocatechin-3-gallate, (+)-Limonene, Myricetin, Quercitrin, Luteolin-7-Glucoside, Morin, Neohesperidin, Hesperidin, Capillarisin, (−)-Epigallocatechin, Luteolin, Hyperoside, Ethyl Myristate, Tamarixetin, Phloretin, Baicalein, Rutin, Baicalin, Apigenin, Naringenin, Hesperetin, (+)-Epicatechin, (−)-Epicatechin-3-gallat, Isoliquiritigenin, Silybin, Vitexin, Genistein, Isorhamnetin, gallic acid, Diosmin, 6-Gingerol, (+)-Taxifolin, Wongonin, Protocatechuic acid, (+)-Catechin, β-naphthoflavone, Embelin, Trans-Cinnamic acid, (−)-Epicatechin, Phloridzin, Puerarin, Umbelliferone, Brij 58, Brij 76, Brij 35, Tween 20, Tween 80, Tween 40, PEG 2000, PEG 400, Pluornic F68, and PEG 4000. The novel, low side-effect compound complex which contains pharmaceutically effective doses of isoniazid (INH), disulfuram (DSF) and/or a third compound, bis-nitrophenyl phosphate (BNPP) can reduce isoniazid (INH)-induced side effects, e.g. hepatotoxicity, etc.

8 Claims, 11 Drawing Sheets

LOW SIDE EFFECT PHARMACEUTICAL COMPOSITION CONTAINING ISONIAZID

BACKGROUND OF THE INVENTION

1. Field of the Invention

The present invention relates to a novel, low side-effect pharmaceutical composition which contains isoniazid (INH).

2. Description of the Prior Art

According to the estimate made by World Health Organization (WHO), nearly one-third of the world populations are infected with tuberculosis (TB) and around eight million new cases were reported every year. In Taiwan, registered new tuberculosis cases have increased dramatically in the past few years, and approximately sixty out of a hundred thousand people were infected at present. However, only three-forth of the patients were receiving the treatments. As indicated by the Department of Health (DOH), 4.2 people died of tuberculosis everyday in Taiwan, and hepatotoxicity and neurological damage, e.g. auditory and optic neuron injury, etc. are common clinical side effects observed in patients treated with TB drugs. Among which, hepatotoxicity is the most common side effect reported. Furthermore, due to the fact that chronic hepatitis B and C are prevailing diseases in Taiwan, if 14,000 people were infected with tuberculosis each year, it is estimated that approximately 2,000 to 3,000 people among those active tuberculosis patients also have chronic liver disorders and require the treatment of tuberculosis. Therefore, the most universal side effect of the tuberculosis treatment, hepatotoxicity, is an iatrogenic disorder that should not be neglected.

Most first line anti-tuberculosis drugs, e.g. isoniazid, pyrazinamide, and rifampin, have potential side effects such as hepatotoxicity. Among those drugs, isoniazid is the most effective, but also the one that can easily induce hepatotoxicity. Isoniazid induced hepatotoxicity has been reported since the late 60's, and roughly 0.1 to 1% of the treated patients showed clinical symptoms of hepatotoxicity (Kopanoff D E et al., Isoniazid-related hepatitis: a U.S. Public Health Service cooperative surveillance study, 1978. Am. Rev Respir Dis 117:991-1001; Nolan C M et al., Hepatotoxicity associated with isoniazid preventive therapy: a 7-year survey from a public health tuberculosis clinic. 1999. JAMA 281: 1014). Moreover, 10 to 20% of those patients exhibited abnormal liver functions in the absence of clinical symptoms, and the first sign of liver injury usually took place two months after the initial treatment of isoniazid (Steele M A et al., Toxic hepatitis with isoniazid and rifampin: A meta-analysis. 1991. Chest. 99: 465).

As shown in FIG. 1, the major pathway of isoniazid metabolism is acetylation to acetylisoniazid by N-acetyltransferase (NAT) followed by rapidly hydrolysis to isonicotinic acid and acetylhydrazine. Acetylhydrazine can be further acetylated into either non-toxic diacetylhydrazine or toxic molecules which include acetyldiazene, acetyloniumion, acetylradical, and ketene etc. by N-acetyltransferase and Cytochrome P450 2E1 (CYP 450 2E1), respectively. Additionally, in the presence of oxygen and NADPH, acetylhydrazine can react with Cytochrome P450 2E1 and produce free radicals, and such oxidative stress can induce cell death. Moreover, both isoniazid and acetylhydrazine can be hydrolyzed to toxic hydrazine by amidase.

Recent studies have indicated that hydrazine (not isoniazid or acetylhydrazine) is most likely to be responsible for INH-induced hepatotoxicity observed in rabbits and rats, and the severity of hepatotoxicity is positively correlate with the plasma concentration of hydrazine (Sarich T C, Youssefi M, Zhou T, Adams S P, Wall R A, Wright J M. Role of hydrazine in the mechanism of isoniazid hepatotoxicity in rabbits. 1996. Arch Toxicol 70: 835-840; Yue J, Peng R X, Yang J, Kong R, Liu J. CYP2E1 mediated isoniazid-induced hepatotoxicity in rats. 2004. Acta Pharmacol Sin. 25: 699-704.). Sarich et al. in 1999 reported that bis-p-nitrophenyl phosphate (BNPP), an inhibitor of amidase, can prevent isoniazid-induced hepatotoxicity by inhibition of hydrazine production (Sarich T C, Adams S P, Petricca G, Wright J M. Inhibition of isoniazid-induced hepatotoxicity in rabbits by pretreatment with an amidase inhibitor. 1999. J Pharmacol Exp Ther. 289: 695-702).

Cytochrome P450 2E1 (CYP2E1) is constitutively expressed in liver and is involved in metabolic pathways of many compounds, e.g. CCl4 and acetaminophen (Lee S S, Buters J T, Pineau T, Fernandez-Salguero P, Gonzalez F J. Role of CYP2E1 in the hepatotoxicity of acetaminophen. 1996. J Biol Chem 271: 12063-12067; Wong F W, Chan W Y, Lee S S. Resistance to carbon tetrachloride-induced hepatotoxicity in mice which lack CYP2E1 expression. 1998. Toxicol Appl Pharmacol. 153: 109-118). Nevertheless, the role of CYP2E1 in isoniazid-induced hepatotoxicity remains unclear. Isoniazid is an inducer of CYP2E1 (Ramaiah S K, Apte U, Mehendale H M. Cytochrome P450 2E1 induction increases thioacetamide liver injury in diet-restricted rats. 2001. Drug Metab Dispos. 29: 1088-1095.). Some studies have suggested that CYP2E1 in liver is involved in the mechanism of isoniazid-induced hepatotoxicity (Yue J, Peng R X, Yang J, Kong R, Liu J. CYP2E1 mediated isoniazid-induced hepatotoxicity in rats. 2004. Acta Pharmacol Sin. 25: 699-704; Huang Y S, Cheen H D, Su W J, Wu J C, Chang S C, Chiang C H, Chang F Y, et al. Cytochrome P450 2E1 genotype and the susceptibility to antituberculosis drug-induced hepatitis. 2003. Hepatology 37: 924-930.). In vitro studies have also suggested that disulfuram (DSF) and its metabolite, diethyldithiocarbamate, are the selective mechanism-based inhibitors for CYP2E1 in human liver microsomes (Guengerich F P, Kim D H, Iwasaki M. Role of human cytochrome P-450 IIE1 in the oxidation of many low molecular weight cancer suspects. 1991. Chem Res Toxicol. 4: 168-179; Hunter A L, Neal R A. Inhibition of hepatic mixed-function oxidase activity in vitro and in vivo by various thiono-sulfur-containing compounds. 1975. Biochem Pharmacol. 24: 2199-2205.). Brady et al. have demonstrated that oral administration of a single dose of disulfuram (DSF) in rats can result in immunoreactive hepatic content and rapidly reduce the activity of CYP2E1 (Brady J F, Xiao F, Wang M H, Li Y, Ning S M, Gapac J M, Yang C S. Effects of disulfuram on hepatic P450 11E1, other microsomal enzymes, and hepatotoxicity in rats. 1991. Toxicol Appl Pharmacol. 108: 366-373.).

Sodhi et al. reported in 1997 that oxidative-stress is one of the factors that contribute to the hepatotoxicity induced by isoniazid and rifampicin in young rats (Sodhi C P, Rana S V, Mehta S K, Vaiphei K, Attari S, Mehta S. Study of oxidative-stress in isoniazid-rifampicin induced hepatic injury in young rats. 1997. Drug Chem Toxicol 20: 255-269). Numerous research focused on identification of appropriate biomarkers so as to evaluate the in vivo rate of oxidation has discovered three types of biomarkers: biomarkers for damage caused by lipid, protein and nucleic acid oxidation. 8-iso-prostaglandin F2α (8-iso-PGF2α) is the product of lipid oxidation of arachidonic acid and is chemically stable. The amount of 8-iso-PGF2α can be used as an indicator for in vivo lipid oxidation and the oxidation is likely related to the production of free radicals, oxidative damage, and antioxidant deficiency (Morrow J D, Hill K E, Burk R F, Nammour T M, Badr K F, Roberts L J, 2nd. A series of prostaglandin F2-like compounds are produced in vivo in humans by a non-cyclooxygenase, free radical-catalyzed mechanism. 1990. Proc. Natl. Acad. Sci. USA 87: 9383-9387; Morrow J D. The isoprostanes: their quantification as an index of oxidant stress status in vivo. 2000. Drug Metab Rev. 32: 377-385.). Presently, many methods are available for measuring the concentration of 8-iso-PGF2α which include enzyme immunoassay (Devaraj S, Hirany S V, Burk R F, Jialal I. Divergence between LDL oxidative susceptibility and urinary F(2)-isoprostanes as measures of oxidative stress in type 2 diabetes. 2001. Clin. Chem. 47: 1974-1979.); radioimmunoassay (Helmersson J, Basu S. F2-isoprostane excretion rate and diurnal variation in human urine. 1999. Prostaglandins Leukot. Essent. Fatty Acids 61: 203-205.); gas-chromatography mass spectrometry (Morrow J D, Roberts L J, 2nd. Mass spectrometric quantification of F2-isoprostanes in biological fluids and tissues as measure of oxidant stress. 1999. Methods Enzymol. 300: 3-12.) and liquid chromatography mass spectrometry (Li H, Lawson J A, Reilly M, Adiyaman M, Hwang S W, Rokach J, FitzGerald G A. Quantitative high performance liquid chromatography/tandem mass spectrometric analysis of the four classes of F(2)-isoprostanes in human urine. 1999. Proc. Natl. Acad. Sci. USA 96: 13381-13386.) etc. In addition, 8-iso-PGF2α in human urine and its metabolite, 2,3-dinor-8-iso-PGF2α, can be extracted by C18 solid phase extraction (SPE) and then apply to LC/MS/MS analysis (Liang Y, Wei P, Duke R W, Reaven P D, Harman S M, Cutler R G, Heward C B. Quantification of 8-iso-prostaglandin-F2α and 2,3-dinor-8-iso-prostaglandin-F2α in human urine using liquid chromatography-tandem mass spectrometry. 2003. Free Radic. Biol. Med 34: 409-418.).

Currently, the available tests for assessing liver function so as to monitor the progress of liver damage and screen for chronic liver diseases include both conventional and quantitative tests. The most common tests used are examining the concentrations of plasma aspartate aminotransferase (AST), plasma alanine aminotransferase (ALT), plasma alkaline phosphatase, and liver metabolites, e.g. bilirubin and albumin etc.; or studying the coagulation factors by measuring the prothrombin time etc. (Carlisle R, Galambos J T, Warren W D. The relationship between conventional liver tests, quantitative function tests, and histopathology in cirrhosis. 1979. Dig. Dis. Sci. 24: 358-362.).

The tests of liver function mostly are based on the turn-over or time-dependent serum concentrations of a test substrate that is metabolized almost exclusively via the liver (hepatic elimination). The clearance of such substrates is determined by the hepatic portal vein and hepatic artery blood flow, as well as by the extraction of these substances by the liver. The hepatic blood flow correlates with the amount of the substances supplied to the liver. On the other hand, its elimination is determined by the hepatic metabolic capacity (Herold C, Heinz R, Niedobitek G, Schneider T, Hahn E G, Schuppan D. Quantitative testing of liver function in relation to fibrosis in patients with chronic hepatitis B and C. 2001. Liver 21: 260-265.).

Galactose is one type of carbohydrates that has high extraction ratio and 90% of its metabolism was processed in liver. In Liver, galactose was epimerized to glucose-1-phosphate by galactokinase and the reaction of galactokinase is the rate-limiting step in galactose metabolism. Due to the high extraction ratio of galatose and related hepatic blood flow, galactose elimination capacity became the most widespread test for examining liver function. At present, no specific test was available for evaluating residual liver function in rats, hence, measuring the metabolism capacity of a definite compound (e.g. galactose) can provide information on both rate-limiting step(s) in liver metabolism and representative value of residual liver function (Keiding S, Johansen S, Tonnesen K. Kinetics of ethanol inhibition of galactose elimination in perfused pig liver. 1977. Scand J. Clin. Lab Invest. 37: 487-494; Keiding S, Johansen S, Winkler K. Hepatic galactose elimination kinetics in the intact pig. 1982. Scand J. Clin. Lab Invest. 42: 253-259).

Galactose elimination capacity (GEC) is a well established quantitative test for assessing human liver function (Lindskov J. The quantitative liver functions as measured by the galactose elimination capacity. I. Diagnostic value and relations to clinical, biochemical, and histological findings in patients with steatosis and patients with cirrhosis. 1982. Acta Med. Scand. 212: 295-302). Nonetheless, the requirement of obtaining multiple blood samples so as to establish a standard curve impedes its clinical applications. Consequently, galactose single point (GSP) test was used instead in numerous studies to assess human liver function. The inventor(s) of the present invention used GSP method to test liver function of patients with chronic hepatitis; liver cirrhosis; and hepatoma, and demonstrated that GSP test can precisely identify these liver disorders (Tang H S, Hu O Y. Assessment of liver function using a novel galactose single point method. 1992. Digestion 52: 222-231). Moreover, previous study has shown that GSP test can be successfully applied to measuring the residual liver function among patients with chronic liver diseases after treatment of promazine and cefoperazone (Hu O Y, Tang H S, Chang C L. The influence of chronic lobular hepatitis on pharmacokinetics of cefoperazone—a novel galactose single-point method as a measure of residual liver function. 1994. Biopharm Drug Dispos 15: 563-576; Hu O Y, Hu T M, Tang H S. Determination of galactose in human blood by high-performance liquid chromatography: comparison with an enzymatic method and application to the pharmacokinetic study of galactose in patients with liver dysfunction. 1995. J. Pharm. Sci. 84: 231-235; Hu O Y, Tang H S, Sheeng T Y, Chen T C, Curry S H. Pharmacokinetics of promazine in patients with hepatic cirrhosis—correlation with a novel galactose single point method. 1995. J. Pharm. Sci. 84: 111-114). In addition, GSP test was recommended by FDA, U.S.A. in the published "Guidance for Industry" to be used as one of the tests for assessing liver function (FDA Center for Drug Evaluation and Research (CDER) Pharmacokinetics in patients with impaired hepatic function: Study design, data analysis, and impact on dosing and labeling. Guidance for Industry, U.S. Department of Health and Human Service. 2003. pp 5). In conclusion, the first line anti-tuberculosis drug, isoniazid, has many side effects and is not well-designed, hence, improvement is much needed.

SUMMARY OF THE INVENTION

In one aspect, the present invention provides a novel, low side-effect pharmaceutical composition comprising isoniazid (INH) and a cytochrome P450 2E1 (CYP2E1) inhibitor and such composition can considerably reduce INH-induced side-effects, particularly hepatotoxicity.

In another aspect of the present invention, it provides a novel, low side-effect pharmaceutical composition comprising isoniazid (INH); disulfuram (DSF), a cytochrome P450 2E1 (CYP2E1) inhibitor; and/or bis-p-nitrophenyl phosphate (BNPP). Such complex can considerably reduce INH-induced side-effects, particularly hepatotoxicity.

To accomplish the goal of the present invention so as to obtain the novel pharmaceutical composition, isoniazid (INH) was used in a rat model to induce hepatotoxicity, and the effects of a cytochrome P450 2E1 (CYP2E1) inhibitor, disulfuram (DSF), and an amidase inhibitor, bis-p-nitrophenyl phosphate (BNPP), on isoniazid-induced hepatotoxicity was examined. In addition to the regular quantitative tests, e.g. hepatotoxicity biomarkers, GSP, and GEC for residual liver function in rats, present invention further utilized an improved liquid chromatography mass spectrometry (LC/MS/MS) to analyze the concentration of serum 8-iso-PGF2α in these rats, and examined the correlation between 8-iso-PGF2α and INH-induced hepatotoxicity.

The novel pharmaceutical composition mentioned above contains pharmaceutically effective doses of isoniazid (INH) and disulfuram (DSF), a cytochrome P450 2E1 (CYP2E1) inhibitor. The cytochrome P450 2E1 (CYP2E1) inhibitor was selected from the following groups of compounds: Nordihydroguaiaretic acid, Trans-Cinnamaldehyde, Daidzein, isovitexin, Kaempferol, disulfuram, β-Myrcene, Quercetin, (−)-Epigallocatechin-3-gallate, Morin, (+)-Limonene, Myricetin, Quercitrin, Luteolin-7-Glucoside, Neohesperidin, Hesperidin, Capillarisin, (−)-Epigallocatechin, Luteolin, Hyperoside, Ethyl Myristate, Tamarixetin, Phloretin, Tamarixetin, Baicalein, Rutin, Baicalin, Apigenin, Naringenin, Hesperetin, (+)-Epicatechin, Isoliquritigenin, (−)-Epicatechin-3-gallate, Silybin, Vitexin, Isorhamnetin, gallic acid, Diosmin, 6-Gingerol, (+)-Taxifolin, Wongonin, Protocatechuic acid, (+)-Catechin, β-naphthoflavone, Embelin, Trans-Cinnamic acid, (−)-Epicatechin, Phloridzin, Puerarin, Umbelliferone, Brij 58, Brij 76, Brij 35, Tween 20, Tween 80, Tween 40, PEG 2000, PEG 400, Pluornic F68, PEG 4000.

The novel pharmaceutical composition with low side effects addressed in the present invention comprising pharmaceutically effective doses of isoniazid (INH), disulfuram (DSF) and/or bis-p-nitrophenyl phosphate (BNPP).

Moreover, the novel pharmaceutical composition with low side effects addressed in the present invention also includes, but is not limited to pharmaceutically acceptable excipients and such excipients can be diluents, fillers, binders, disintegrating agents or lubricants, etc.

BRIEF DESCRIPTION OF THE DRAWINGS

The foregoing summary, as well as the following detailed description of the invention, will be better understood when read in conjunction with the appended drawings. It should be understood, however, that the invention is not limited to the preferred embodiments shown.

In the drawings:

FIG. 3A shows the normal hepatic tissue from control group (H&E staining, 400×), FIG. 3B shows central portal vein (V) hepatocyte damage and vacuolization (H&E staining, 400×), FIG. 3C is the electron microscope scan of rat liver sections from control group, Nu: nucleus (9,000×), FIG. 3D shows electron microscope scan of rat liver sections from INH group. In compare with control group, the rough endoplasmic reticulum (rER) in rats treated with INH increased significantly, Nu: nucleus (9,000×).

DETAILED DESCRIPTION OF THE PREFERRED EMBODIMENT

Figure 1:
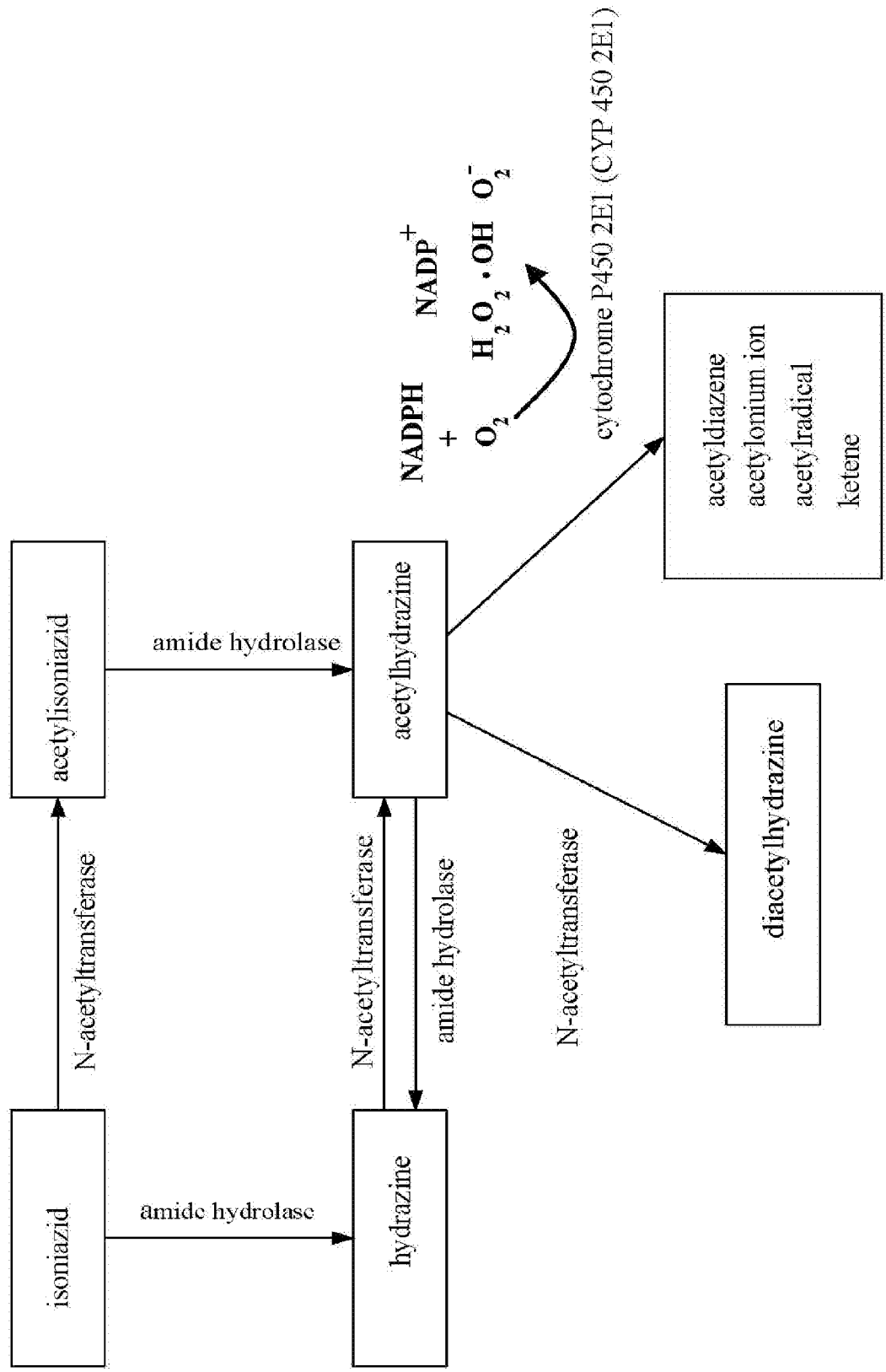
FIG. 1 shows the major pathways of isoniazid (INH) metabolism in liver.

The present invention will now be described more specifically with reference to the following embodiments, which are provided for the purpose of demonstration rather than limitation.

Example 1

Animal Study of INH Treatment Combined with the CYP2E1 Inhibitor, Disulfuram (DSF) and/or Bis-P-Nitrophenyl Phosphate (BNPP)

1. Materials and Methods

All organic solvents are HPLC grade and purchased from Tedia (Fairfield, Ohio, USA) and corn oils were purchased from Sigma (St. Louis, Mo., USA). 8-iso-PGF2α and radioactive 8-iso-PGF2α were obtained from Cayman (Ann Arbor, Mich., USA). Galactose injection solution was prepared by South Photochemical Pharmaceutical Co., Ltd by dissolving 400 g of galactose in 1 L isotonic buffering distilled water.

2. Animals

Male SD (Sprague-Dawley) rats weighing 320 to 350 g were purchased from National Laboratory Animal Center (Taiwan) and study was performed according to the animal study guidance published by Nation Health Research Institute (NHRI). Throughout the experiment, the rats were housed in air-conditioned and temperature-adjusted cages with a 12-h light/dark cycle and free access to water and food. The body weight of the rats was monitored throughout the experiment. Rats were anesthetized with sodium pentobarbital intraperitoneally (i.p.) at the dose of 50 mg/kg and galactose was injected intravenously through a polyethylene catheter positioned in internal jugular vein. The catheter was positioned by cut-down technique and its end was embedded under the skin behind the neck. After the surgery, the rats were fasted overnight during the recovery period (about 16 hours) with unrestricted water access 3. Experimental Procedures Animals were randomized into one of five groups, each involving three treatments. The first treatment involved either a BNPP injection of 25 mg/kg or a BNPP vehicle (VEH1) injection (saline). BNPP was dissolved in saline (0.9% NaCl) after heating to approximately to 60° C., and after cooling, intraperitoneally (i.p.) injected at a volume of 1 mg/kg. The second treatment involved injections of either 100 mg/kg DSF or DSF vehicle (VEH2, corn oil). DSF was dissolved in corn oil and i.p. injected at a volume of 1 mg/kg. The third treatment involved injections of INH (25 mg/kg) or INH vehicle (VEH3, saline). INH was dissolved in saline (0.9% NaCl), and i.p. injected at a volume of 1 mg/kg. The first treatment (BNPP or VEH1) was administered 30 minutes before the third treatment (INH or VEH3), and the second treatment (DSF or VEH2) was administered 15 minutes before the third treatment (INH or VEH3).

The five treatment groups are:
(1) Normal control group (NC, n=12): continuously injections of VEH1, VEH2 and VEH3 intraperitoneally once every day for 21 days;
(2) INH group (INH, n=7): continuously injections of INH, VEH1 and VEH2 intraperitoneally once every day for 21 days;
(3) BNPP-INH group (BNPP-INH, n=7): continuously injections of BNPP, INH and VEH2 intraperitoneally once every day for 21 days;
(4) DSF-INH group (DSF-INH, n=7): continuously injections of DSF, INH and VEH1 intraperitoneally once every day for 21 days;
(5) BNPP-DSF-INH group (BNPP-DSF-INH, n=7): continuously injections of BNPP DSH and INH intraperitoneally once every day for 21 days;

Galactose elimination capacity (GEC) test was performed 16 hours after the rats were sacrificed at the end of 21 days-treatment to measure the liver function.

4. Blood Sampling

After 21 days treatment, the rats were sacrificed with ether and blood samples collected in test tubes containing EDTA by dorsal aorta extract. The blood samples were centrifuged at 13,000 g for 15 min at 4° C. and plasma was aliquot into eppendorf tubes and stored at −80° C.

5. Biochemical Analysis

Hepatocellular damage was quantified by measuring both peak plasma aspartate aminotransferase (AST) and alanine aminotransferase (ALT) activities. AST and ALT activities are the most common biomarkers for hepatotoxicity and were measured by Synchron LXi 725 system (Beckman Instruments, USA).

6. Light Microscopy and Electron Microscopy

After the rats were sacrificed, the livers were subjected to histology analysis. Liver samples were fixed with 10% phosphate-buffered formalin and then, dehydrated and embedded in paraffin. Tissue was sectioned at 5 mm thick and stained with hematoxylin and eosin and Periodic acid Schiff stain (PAS) simultaneously, and results were observed under a light microscope. In addition, liver sections were washed with 0.1M cacodylate buffer (pH 7.4) and then fixed with 20% aqueous osmium tetroxide for 1 hour. Dehydrated and embedded in Spurr resin, and ultra-thin sections were obtained by using a diamond blade and double-stained with uranyl acetate and lead citrate, and sections were further examined under a Transmission Electron Microscope, Hitachi 600 (Hitachi Co., Japan).

7. Extraction and Quantification of 8-iso-PGF2α

All isomers of PGF2α were dissolved or diluted in adequate amount of ethanol and after aliquot, stored at −70° C. As an internal standard, 10 ng of 8-iso-PGF2α-d4 was mixed with 0.5 ml of plasma in a glass tube and was then purified by a C18 Solid-Phase Extraction column (J. T. Baker, MA, USA). Sample eluants were evaporated under a stream of nitrogen and re-dissolved in 50 µl acetonitrile:water (15:85 v/v) solution followed by vortex for 30 seconds and 10 µl extract was further analyzed with a LC/MS/MS system.

8. Liquid Chromatography Mass Spectrometry (LC/MS/MS) Analysis

The HPLC system used includes two Shimadzu LC-10ADvP pumps, one Shimadzu system control and one Shimadzu autosampler (Shimadzu, Japan). HPLC purification of the extract by C18 column (mesh size 5-µm, diameter 50×2.1 mm) using 2 mM ammonium acetate/acetonitrile, ACN gradient as mobile phase (t=0 min, 15% ACN; t=6 min, 70% ACN; t=7 min, 90% ACN; t=8 min, 90% ACN; t=8.5 min, 15% ACN). The flow rate of LC/MS/MS was maintained at 200 µl/min and the total time of purification was 13.5 minutes. Such HPLC system was connected to a triple stage quadrupole mass spectrometer (API3000, Applied Biosystem, Foster City, Calif., USA) and is equipped with a Turbo-IonSpray ionization source, and uses negative electrospray for ionization. Such spectrophotometer uses diffusion of standard solution of 200 ng/ml 8-iso-PGF2α or 8-iso-PGF2α-d4 to optimize the mode for multiple reaction monitoring (MRM). Ion pairs, m/z 353/193 and m/z 357/197, were used to monitor 8-iso-PGF2α and 8-iso-PGF2α-d4, respectively.

After quantification, linear calibration curve was constructed by plotting 6 8-iso-PGF2α concentrations (C) and area (Y) of 8-iso-PGF2α to 8-iso-PGF2α-d4 ratio, and the obtained correlation coefficient (r) is 0.999. Plasma 8-iso-PGF2α linearity range from 0.1 to 2.5 ng/ml and its regression equation is Y=−0.0517C+0.823 ng/ml. The measured results were calculated using deuterated 8-iso-PGF2α as internal control, and inter-batch precision and accuracy of the standard curve were evaluated by Back-Calculation on 6 individual measurements of internal control samples and the relative errors range from −5.06% to 3.13%.

9. Quantitative Tests of Liver Function

All rats were subjected to GSP and GEC tests. Galactose was injected intravenously within 30 seconds (0.4 g/ml, 0.5 g/kg BW) and blood samples were collected once at 5, 10, 15, 30, 45 and 60 minutes post injection by tail vein puncture. The amount of galactose was measured by the concentration of colorimetric galactose dehydrogenase and the tested concentrations ranged from 50 to 1,000 µg/ml. The within-day variation of each concentration was calculated by percentage of standard deviation and coefficient of variation (CV). Day to day variation was determined by examining the slopes and the intercepts of the calibration curves and GEC was calculated by the following equation, and said equation was modified from Tygstrup's equation (Tygstrup N. The Galactose Elimination Capacity in Control Subjects and in Patients with Cirrhosis of the Liver. 1964. Acta Med. Scand 175: 281-289).

$$GEC = \frac{D}{TC = 0 + 7}(mg/kg \cdot min)$$

D is the injection volume of galactose; Tc=0 is the time required for galactose to reach concentration of 0 and was obtained from blood concentrations-time curve linear regression 20 to 60 min post injection (usually at 2.22 mmol/L); 7 is the correction value of in vivo uneven distribution amended in accordance with rules of thumb; and GSP value was the blood concentration of galactose 60 min after the 30-second injection.

10. Statistical Analysis

All representative values are mean±standard deviation (SD) and were analyzed by one-way analysis of variance (ANOVA) and P values was determined for significant differences. Calculation was made by using Statistical Package of the social Science program (version 13, SPSS Inc.) software and followed by post hoc test so as to compare the least significant difference and confirm the significant differences among groups, the average of significant difference is $P<0.05$.

Results

1. Biochemical Analysis

Figure 2:
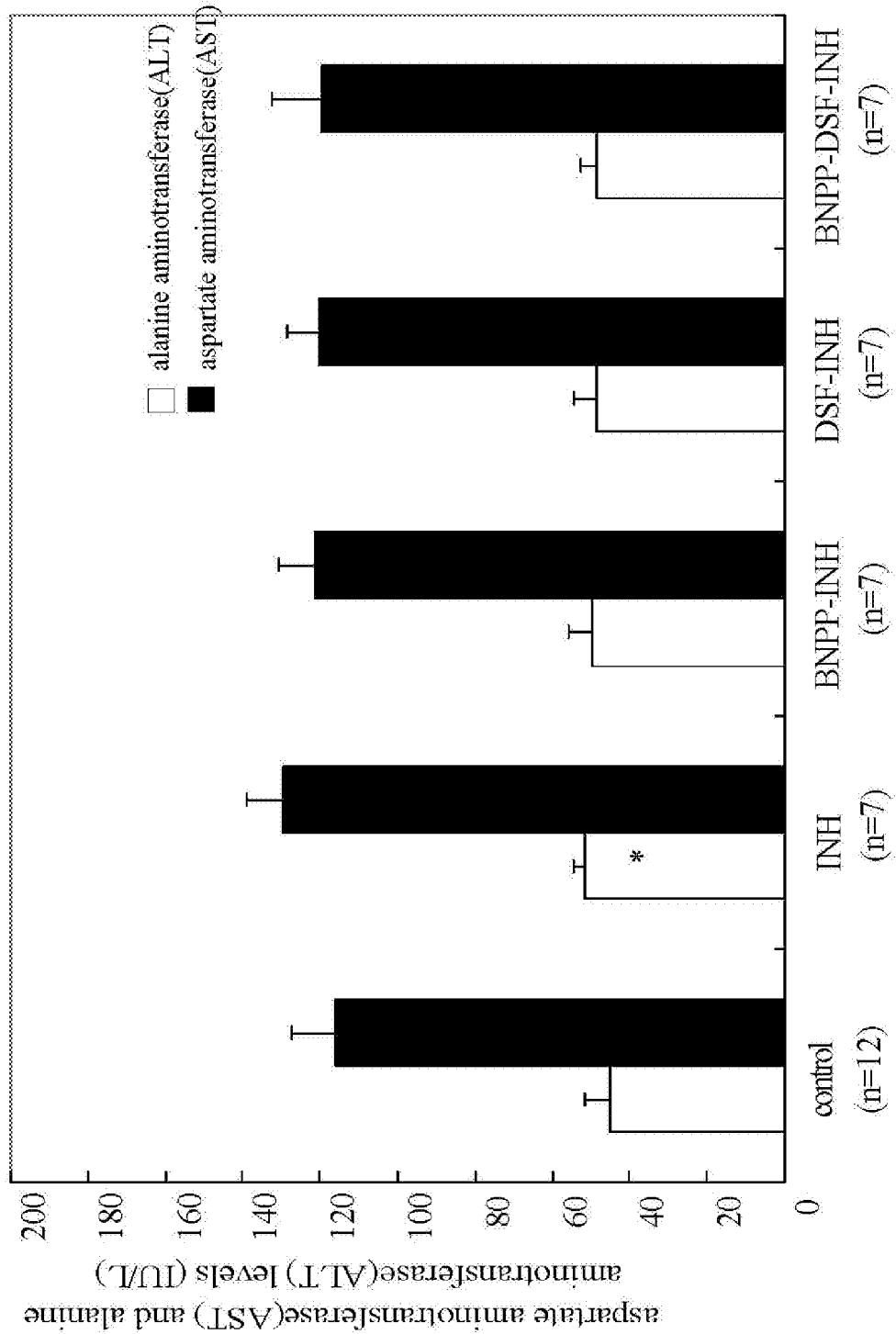
FIG. 2 shows the activities of AST and ALT in rats treated with INH, BNPP-INH, DSF-INH or BDPP-DSF-INH. Values represent the mean±SD, * indicates significant difference was observed between experimental and control groups, $P<0.05$.

At the end of the study, no significant differences was found between experimental and control animal groups in their body weight and relative liver weight. Biochemical analysis as shown in FIG. 2, peak plasma AST and ALT activities were significantly increased above control levels only in the INH group (the plasma AST activities were 116±11 IU/L and 129±10 IU/L in the control and the INH groups, respectively, ($p<0.05$); and the plasma ALT activities were 44±6 IU/L and 52±3 IU/L in the control and the INH groups, respectively, ($p<0.05$)) which demonstrated that biochemical hepatocellular injury was induced in the INH group whereas the concentrations of plasma aminotransferases in the control, BNPP-INH and BNPP-DSF-INH groups remained normal.

2. Histopathology

Figure 3:
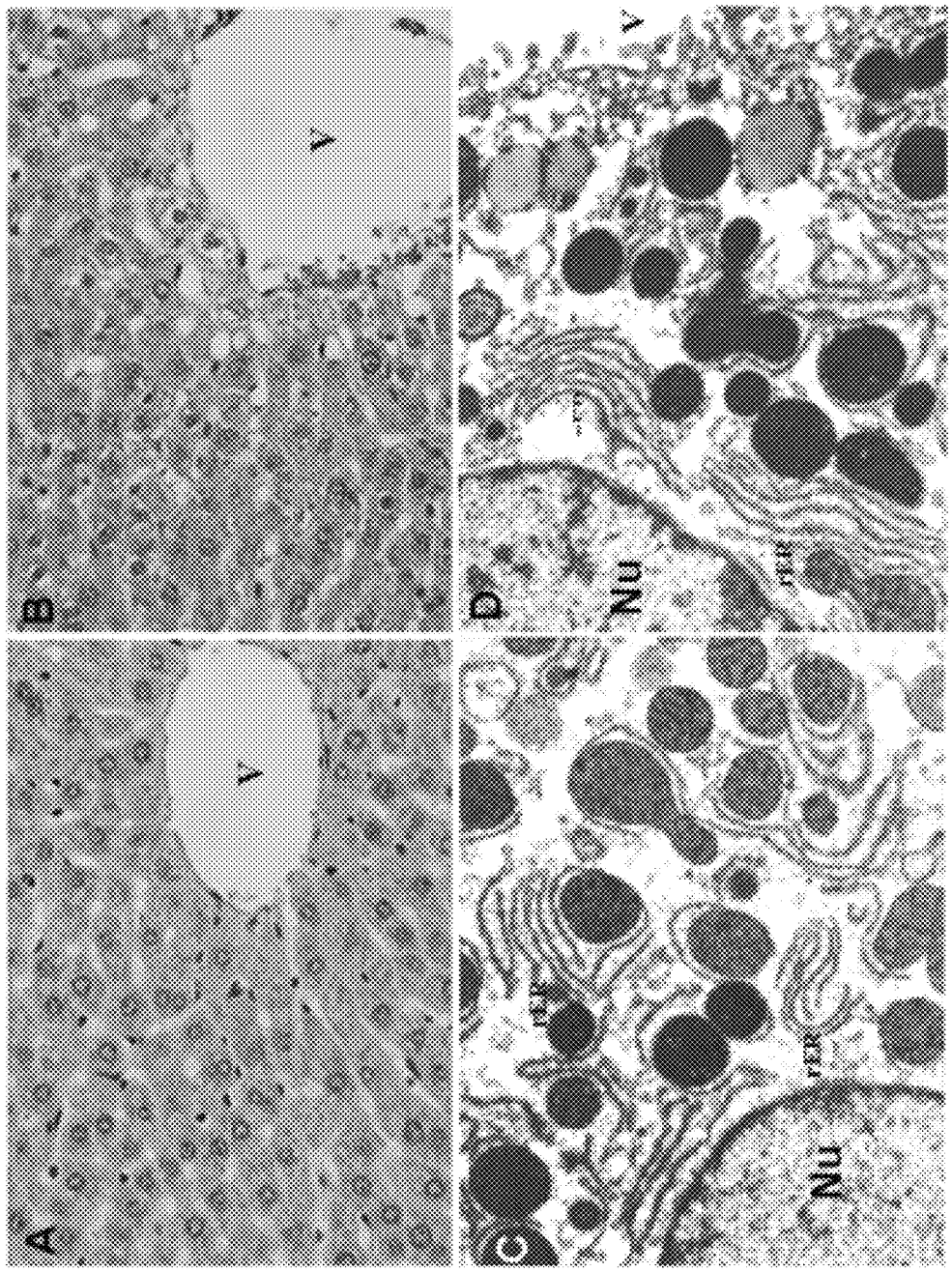
FIG. 3 shows the H&E staining of liver sections of rats treated with INH.

After daily i.p. injections of 150 mg/kg for three weeks, rats in the INH group showed hepatocellular damage. In contrary, liver structure remained normal in the control group. As shown in FIG. 3, hepatocytes in liver parenchyma from the control group were arranged inside of mesh plate in the radiation from the centrilobular portal vein, and hepatic sinusoids were found between two anastomosing plates. Liver sections from the INH group were shown in FIG. 3B, and hepatocytes surrounding the portal vein were fragmented and shown vacuolization. However, no hepatic necrosis was observed from the EM results. Comparison of the control group and the INH group (as shown in FIG. 3) indicated that hepatocytes rough endoplasmic reticulum (rER) from the INH group increased significantly. Previous studies have indicated that INH is a potent cytochrome P450 2E1 (CYP2E1) inducer (Ryan D E, Ramanathan L, Iida S, Thomas P E, Haniu M, Shively J E, Lieber C S, et al. Characterization of a major form of rat hepatic microsomal cytochrome P-450 induced by isoniazid. 1985. J. Biol. Chem. 260: 6385-6393), and CYP2E1 can cause the production of superoxide and hydroxyl radicals (Ekstrom G, Ingelman-Sundberg M. Rat liver microsomal NADPH-supported oxidase activity and lipid peroxidation dependent on ethanol-inducible cytochrome P-450 (P-450IIE1). 1989. Biochem. Pharmacol. 38: 1313-1319) and can increase ER function (Sodhi C P, Rana S V, Mehta S K, Vaiphei K, Attri S, Thakur S, Mehta S. Study of oxidative stress in isoniazid-induced hepatic injury in young rats with and without protein-energy malnutrition. 1996. J Biochem Toxicol. 11: 139-146.). Therefore, current results is consistent with prior research and liver injury in other tested groups including BNPP-INH, DSF-INH, and BNPP-DSF-INH showed no significant differences in compared with the control group (data not shown).

3. Quantification of 8-iso-PGF2α from the Blood Samples

Under the mode of electrospray ionization, the maximum mass-to charge ratios of 8-iso-PGF2α and 8-iso-PGF2α-d4 are 353 (m/z) and 357 (m/z) ions, respectively. These negative charged ions were produced after numerous collisions and the molecular structures and mass spectrum of these two target compounds were shown in FIG. 4. In addition to the fact that the daughter ions of 8-iso-PGF2α-d4 is four times higher than 8-iso-PGF2α's, fragmentation patterns are very similar between 8-iso-PGF2α and 8-iso-PGF2α-d4 which indicated that most stable daughter ions were produced from A chain, and four deuterium atoms were labeled on such A chain. The most intensive daughter ions of 8-iso-PGF2α and 8-iso-PGF2α-d4 are (m/z)193 and (m/z)197 ions. FIG. 5 shows the LC/MS/MS chromatograph of 100 pg 8-iso-PGF2α and 250 pg/ml 8-iso-PGF2α-d4 (standard internal control) and a typical blood sample using MRM (multiple reaction monitor) mode. After injection of 1ng 8-iso-PGF2α-d4 as internal control, such control and blood samples were both purified by SEP and further analyzed by LC/MS/MS as mentioned earlier.

4. Concentrations of Plasma 8-iso-PGF2α

Figure 6:
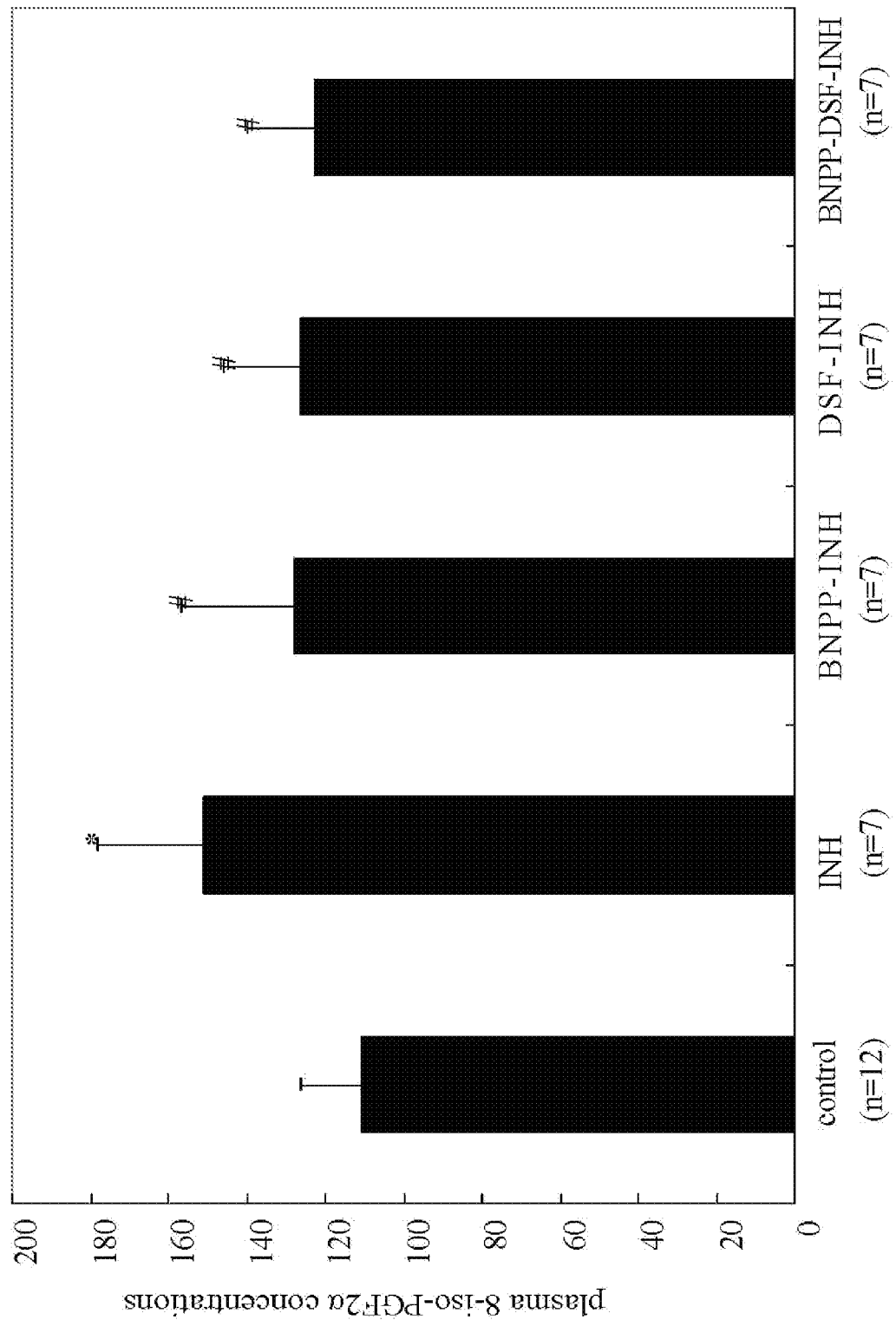
FIG. 6 shows the plasma 8-iso-PGF2α concentrations of rats treated with control, INH, BNPP-INH, DSF-INH and BNPP-DSF-INH. Values represent the mean±SD, * indicates significant differences between experimental and control groups, $P<0.001$ and # indicates significant differences between experimental and control groups, $P<0.05$.

Plasma 8-iso-PGF2α is an indicator for oxidative stress. As shown in FIG. 6, in compare with the control group, plasma 8-iso-PGF2α increased significantly in the INH group (the plasma concentrations of 8-iso-PGF2α in the INH and the control groups are 151±26 pg/ml and 110±15 pg/ml, respectively, $p<0.001$) and BNPP-INH, DSF-INH, and BNPP-DSF-INH groups all showed considerably reduction of INH-induced 8-iso-PGF2α (the plasma concentrations of 8-iso-PGF2α in the BNPP-INH, DSF-INH, and BNPP-DSF-INH groups are 128±29 pg/ml, 126±20 pg/ml and 123±17 pg/ml) and plasma 8-iso-PGF2α concentration in the INH group is 151±26 pg/ml, $p<0.005$. Interestingly, no significant differences were observed among the control, BNPP-INH, DSF-INH, and BNPP-DSF-INH groups. Moreover, INH combined with either BNPP or DSF did not further reduce the plasma concentration of 8-iso-PGF2α.

5. Residual Liver Function Test

Figure 7:
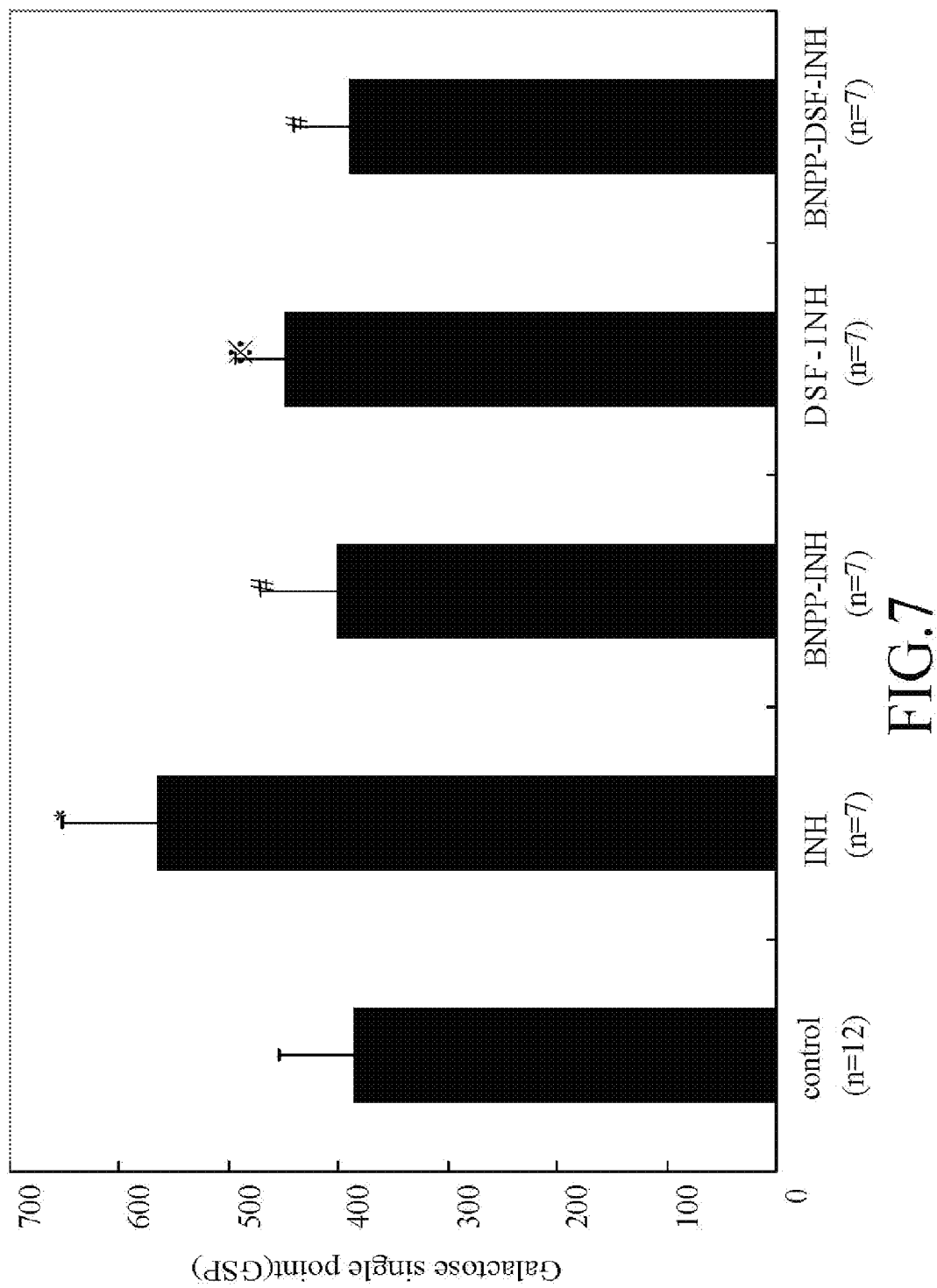
FIG. 7 shows the GSP values of rats treated with control, INH, BNPP-INH, DSF-INH and BNPP-DSF-INH. Values represent the mean±SD, * indicates significant differences between experimental and control groups, $P<0.001$; # indicates significant differences between experimental and control groups, $P<0.001$; and ✗ indicates significant differences between experimental and control groups, $P<0.005$.

As shown in FIG. 7, the GSP test values between the control group and the INH group are significantly different (GSP values of the control and INH groups are 384±69 μg/ml and 565±87 μg/ml, respectively). In addition, GSP values of the BNPP-INH, DSF-INH, and BNPP-DSF-INH groups are 401±70 μg/ml, 449±45 μg/ml, and 388±53 μg/ml. The BNPP-INH, DSF-INH, and BNPP-DSF-INH groups are all significantly different from the INH group ($p<0.001$, $p<0.005$, and $p<0.001$). Furthermore, GSP value was elevated considerably in the INH group, whereas groups treated with combination drugs of INH and BNPP, INH and DSF, or INH and BNPP-DSF can resist such increase. On the other hand, compare to the DSF-INH group, INH combined with BNPP and DSF can significantly reduce INH-induced hepatotoxicity, though no statistical difference was observed ($p=0.1$). Also, no statistical differences were found among the GSP values of the control, the BNPP and the BNPP-DSF groups.

Figure 8:
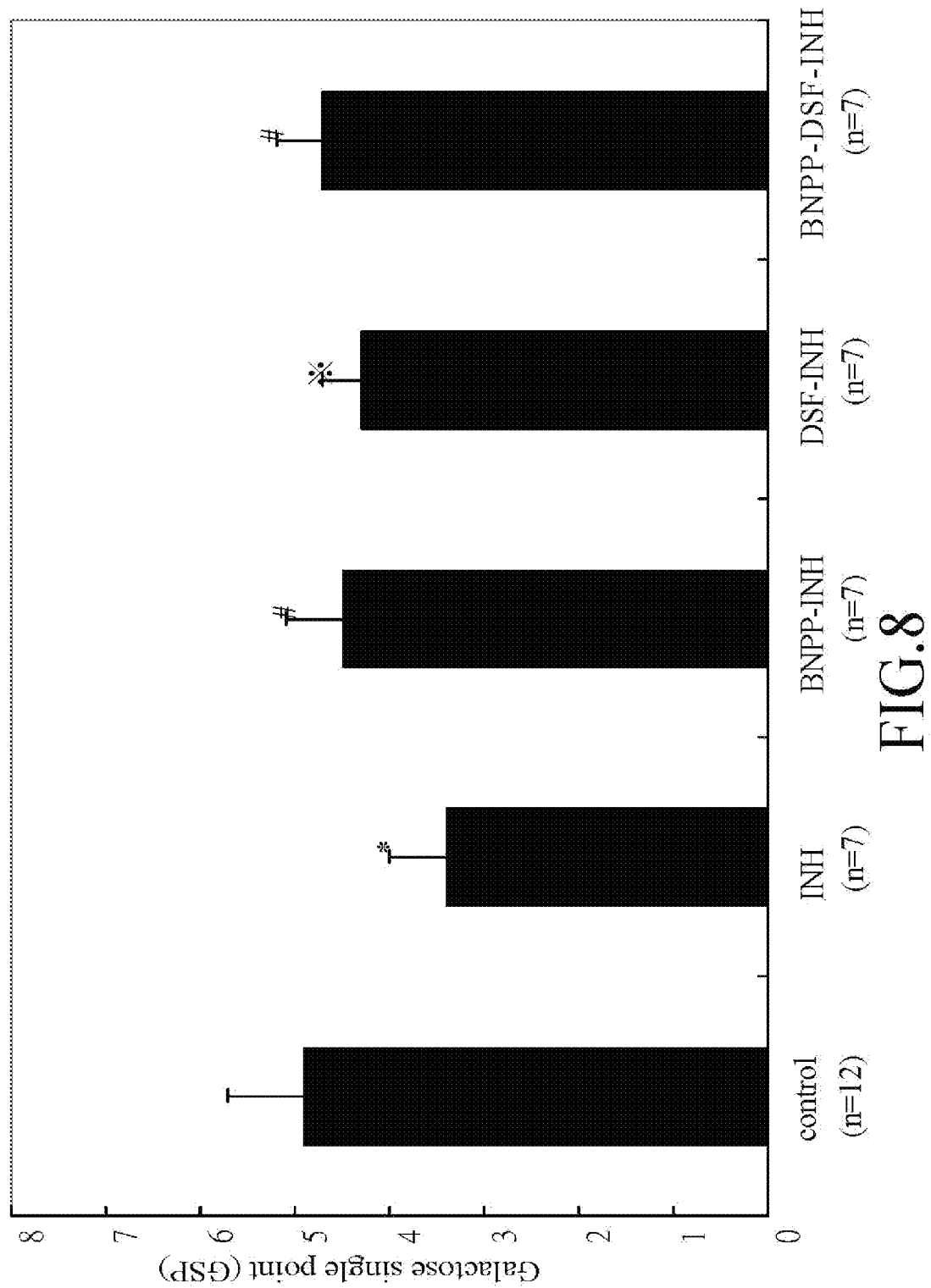
FIG. 8 shows the GEC values of rats treated with control, INH, BNPP-INH, DSF-INH and BNPP-DSF-INH. Values represent the mean±SD, * indicates significant differences between experimental and control groups, $P<0.001$; # indicates significant differences between experimental and control groups, $P<0.005$; and ✗ indicates significant differences between experimental and control groups, $P<0.005$.

Similar results were also observed in GEC tests. As shown in FIG. 8, GEC values are significantly reduced in the INH group compare to the control group (the GEC values of the INH and the control groups are 3.4±0.6 mg/min·kg and 4.9±0.8 mg/min·kg, p<0.001, respectively). Additionally, GEC values of the BNPP-INH, DSF-INH, and BNPP-DSF-INH groups are 4.5±0.6 mg/min·kg, 4.3±0.4 mg/min·kg and 4.7±0.5 mg/min·kg. All three groups exhibited significant differences from the INH group (p<0.005, p<0.05, and p<0.005). GEC values reduced noticeably in the INH group, whereas the combination of BNPP and INH; DSF and INH; and BNPP-DSF and INH can restore such reduction. Moreover, compare to DSF-INH group, INH combined with both BNPP and DSF tend to increase the GEC value (the GEC values of the DSF-INH and BNPP-DSF-INH groups are 4.3±0.4 mg/min·kg and 4.7±0.5 mg/min·kg, respectively, p=0.29). In addition, no statistical differences were found among the GSP values of the control, the BNPP, the DSF, and the BNPP-DSF groups.

Figure 9:
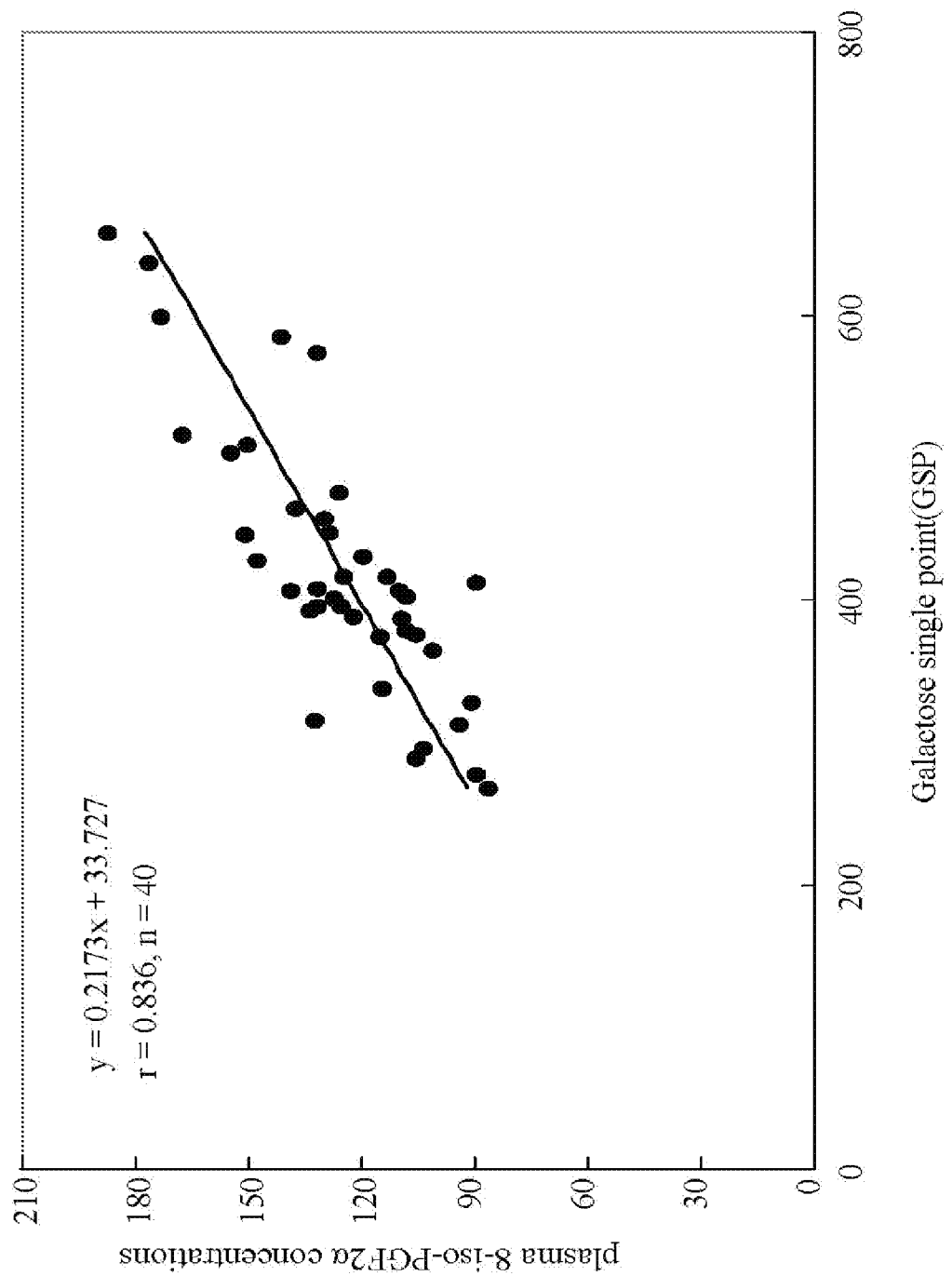
FIG. 9 is the statistical analysis results and demonstrated that GSP test values highly correlate with the concentration of 8-iso-PGF2α in rats treated with control, INH, BNPP-INH, DSF-INH and BNPP-DSF-INH.
Figure 10:
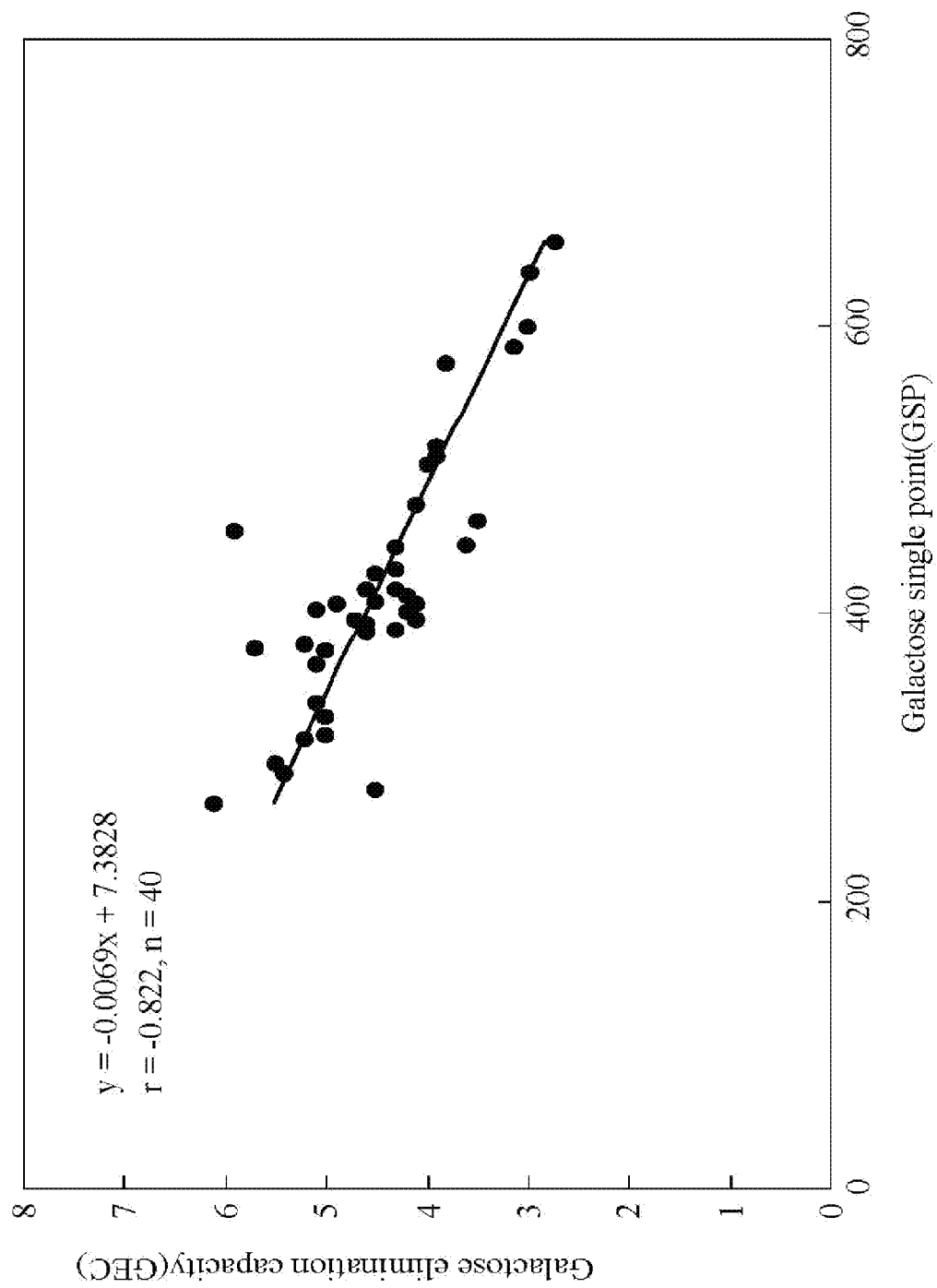
FIG. 10 is the statistical analysis results and demonstrated that GSP test values highly correlate with GEC test values in rats treated with control, INH, BNPP-INH, DSF-INH and BNPP-DSF-INH.

In order to confirm the concentrations of plasma AST, plasma ALT and plasma 8-iso-PGF2α and to verify the correlation between quantitative tests for liver function (e.g. GSP and GEC tests), several analyses were performed and the results have suggested that the GSP values are highly correlate with plasma 8-iso-PGF2α concentration (as shown in FIG. 9), the co-efficient is 0.836; the GSP values are highly correlate with the GEC values, (p<0.001), the co-efficient is −0.822; and finally, the GEC values are also highly correlate with plasma 8-iso-PGF2α concentration, the co-efficient is −0.743 (p<0.001). On the other hand, GSP values, GEC values and plasma 8-iso-PGF2α concentration are not correlated with either AST or ALT concentrations (as shown in table 1).

TABLE 1

Correlations between biochemical analysis and GSP, GEC and 8-iso-PGF$_{2\alpha}$

|  | GSP | GEC | 8-iso-PGF2α |
|---|---|---|---|
| AST | r = 0.114 | r = −0.111 | r = 0.217 |
| ALT | r = 0.016 | r = 0.039 | r = 0.035 |
| 8-iso-PGF2α | r = 0.836* | r = −0.743* | r = 1* |

Statistically analyzed by Pearson's correlation coefficient
*p < 0.00

Example 2

Screening of Cytochrome P450 2E1 (CYP2E1) Inhibitors-cDNA Expressed Human Cytochrome P450 2E1 (CYP2E1)

1. Materials and Methods

CYP2E1 High Throughput Inhibitor Screening Kit (BD Bioscience, USA) was used to screen the cytochrome P450 (CYP2E1) inhibitors from 22 Chinese herbal ingredients and 10 excipients and microsomal cytochrome P450 (CYP2E1) was synthesized from cDNA (BD Bioscience, USA). The principle of the screening kit is to measure the percentage of CYP2E inhibition, after adding the test sample to substrate MFC (7-Methoxy-4-trifluoromethyl coumarin) and cytochrome P450 (CYP2E1), by measuring the synthesis of standard CYP2E1 metabolite (HFC, 7-Hydroxy-4-trifluoromethyl coumarin) and use control HFC as baseline.

All test samples were dissolved in acetonitrile and tested for their effects on inhibition of CYP2E1 at different concentrations: Chinese herbal ingredients (66 µM, 33 µM, 16.5 µM) and excipients (0.167%, 0.08%, 0.042%, w/v). The tested results of Chinese herbs and excipients were listed in FIG. 3 and FIG. 4, respectively.

The materials used for CYP2E1 High Throughput Inhibitor Screening Kit included:
(1) CYP2E1+P450 Reductase+Cytochrome b5: 100 mM potassium phosphate (pH 7.4) with 1.3 nmol P450 and p-Nitrophenol dehydrogenase.
(2) Control proteins: 15 mg/mL control protein was dissolved in 100 mM potassium (pH7.4).
(3) Buffer solution: 0.5M potassium phosphate (pH 7.4).
(4) Stop solution: 0.5 M Tris Base.
(5) Cofactors: contains 1.3 mM NADP+, 66 mM MgCl2 and 66 mM Glucose 6-Phosphate.
(6) Glucose 6-Phosphate dehydrogenase: 40 units/ml in 5 mM Sodium Citrate Buffer (pH 7.5).
(7) MCF (7-Methoxy-4-trifluoromethyl coumarin), a fluorescence substrate, was dissolved in 50 mM acetonitrile.
(8) DDTC (Diethyldithiocarbamic acid): a CYP2E1 selective inhibitor (experimental group), 20 mM DDTC was dissolved in acentoitrile.
(9) HFC (7-Hydroxy-4-trifluoromethyl coumarin): a CYP2E1 metabolite standard, 0.25 mM HFC was dissolved in 0.1M Tris (pH 9.0).
(10) NADPH-Cofactor Mix: 187.5 µl cofactors, 150 µl G6PDH (glucose 6-Phosphate dehydrogenase solution) and 100 µl control protein in 14.56 µl sterilized water.
(11) Cofactor/acentonitrile mix: 660 acentonitrile was added into 9.93 ml NADPH-cofactor mix.
(12) Enzyme/Substrate Mix: 5.94 ml sterilized water, 50 µl HTS-706(CYP2E1, 2 µM P450 content), and 28 µl 50 mM MFC (7-Methoxy-4-trifluoromethyl coumarin (fluorescence substrate) were added to 5.94 ml sterilized water.

2. Selection of cytochrome P450 2E1 (CYP2E1) inhibitors

The procedures of selection of cytochrome P450 2E1 (CYP2E1) inhibitors from Chinese herbal ingredients and excipients using the CYP2E1 High Throughput Inhibitor Screening Kit (BD Bioscience, USA) are:

Preparation of Controls:

(1) Preparation of Control Groups

149 µl NADPH-Cofactor Mix and 1 µl 20 mM DDTC were added to the #1 well in a 96-well plate and mixed thoroughly, Add 100 µl Cofactor/acetonitrile mix to #2 to #12 wells, and well #1 to #8 are positive control. Well #9 and 10 are control and well #11 and #12 are blank, Perform serial dilution from well #1 to #8 by transferring 50 µl from well #1 and transfer to well #2; after mixed thoroughly, transferring 50 µl from well #2 and transfer to well #3 and so on to well #8 and remove 50 µl from well #8 and the diluted concentrations are: 66.6, 22.2, 7.4, 2.47, 0.82, 0.27, 0.091 and 0.03 µM, (2) Preparation of Experimental Groups:

149 µl NADPH-Cofactor Mix and 1 µl 20 mM Chinese herbal ingredients or 1 µl 25% (w/v) excipients were added to the well #1 and #2, respectively, in a 96-well plate and mixed thoroughly, Transfer 50 µl from well #1 and #2 and added to well #3 and mixed thoroughly (triplicate for each sample), (3) Initiation and Termination of the Reaction:

The 96-well plate was incubated at 37° C. for 10 min,

100 µl of Enzyme/Substrate Mix was added to every well and mixed thoroughly except the blank wells, The 96-well plate was incubated at 37° C. for 40 min, 75 μl Stop Solution was added to every well and mixed thoroughly, Immediately add 100 μl Enzyme/Substrate Mix to blank wells and mixed thoroughly, Measure with a Fluoroskan Ascent FL (Thermo Electron Corporation, Finland) with excitation at 405 nm and emission at 538 nm, (4) Data Analysis:

The fluorescence was transverse into CYP 2E1 metabolite standard (HFC) concentration (pmol) and the percentage (%) of CYP 2E1 inhibition was calculated using control as baseline by following equation:

$$CYP2E1\ \text{inhibition}\ (\%) = 1 - \frac{\text{Sample } HFC}{\text{Control } HFC}$$

Results

1. Positive Controls

CYP 2E1 inhibition of positive controls (DDTC) was shown in table 2. Inhibition of CYP 2E1 reached 97.555% when DDTC was at 66.6 μM concentration (that is 0.167%, w/v). This is the highest tested concentration for Chinese herbal ingredients, and 0.167% (w/v) is the highest tested concentration for excipients.

TABLE 2

Inhibition of CYP 2E1 (%) by positive controls

| DDTC concentration (μM) | HFC synthesis (pmol) | Inhibition of CYP 2E1 (%) |
|---|---|---|
| 0 (control) | 222.00 | 0 |
| 0.03 | 256.00 | — |
| 0.091 | 202.00 | 8.71 |
| 0.27 | 151.71 | 31.52 |
| 0.82 | 126.14 | 43.06 |
| 2.47 | 55.18 | 75.09 |
| 7.4 | 21.08 | 90.49 |
| 22.2 | 15.10 | 93.19 |
| 66.6 | 5.42 | 97.55 |

2. Inhibition of CYP 2E1 in Test Groups

The CYP 2E1 inhibition activity of various Chinese herbal ingredients was shown in FIG. 3 and different guiding drugs have different inhibition effects at various concentrations (66 μM, 33 μM, 16.5 μM). Among those tested guiding drugs, Nordihydroguaiaretic acid at 66 μM exhibited the best inhibition activity (97.99±0.66%).

TABLE 3

Inhibition of CYP 2E1 (%) by Chinese herbal ingredients

| Chinese herbal ingredients | Inhibition of CYP 2E1 (%) Tested concentration | | |
|---|---|---|---|
| | 66 μM | 33 μM | 16.5 μM |
| Control | 0 | 0 | 0 |
| Positive control (DDTC) | 97.55 ± 1.862 | | |
| Nordihydroguaiaretic acid | 97.99 ± 0.66 | 92.36 ± 2.20 | 76.52 ± 3.86 |
| (−)-Epigallocetechin-3-gallate | 97.56 ± 0.18 | 96.47 ± 0.64 | 92.56 ± 0.46 |
| Capillarisin | 76.12 ± 1.89 | 60.54 ± 5.91 | 49.05 ± 5.18 |
| Kaempferol | 70.63 ± 2.53 | 70.04 ± 3.75 | 71.87 ± 1.14 |
| Phloretin | 66.84 ± 4.79 | 54.69 ± 2.84 | 42.04 ± 3.63 |
| disulfiram | 66.54 ± 2.55 | 60.55 ± 5.70 | 57.89 ± 3.91 |
| Hesperetin | 54.75 ± 1.37 | 43.29 ± 0.82 | 32.10 ± 5.80 |
| 6-Gingerol | 51.89 ± 3.33 | 39.83 ± 2.32 | 30.13 ± 2.67 |
| gallic acid | 48.24 ± 4.20 | 42.74 ± 7.36 | 35.59 ± 10.03 |
| Isoliquritigenin | 47.83 ± 5.36 | 46.27 ± 3.28 | 39.08 ± 2.75 |
| Narigenin | 41.84 ± 3.51 | 36.82 ± 3.97 | 25.11 ± 7.60 |
| (+)-Taxifolin | 34.54 ± 3.47 | 23.80 ± 5.84 | 22.58 ± 11.69 |
| Wongonin | 23.48 ± 2.59 | 21.87 ± 1.90 | 15.64 ± 7.82 |
| Protocatechuic acid | 22.75 ± 4.07 | 19.95 ± 8.95 | 25.66 ± 12.74 |
| (+)-Catechin | 16.45 ± 9.67 | 33.83 ± 8.76 | 41.53 ± 7.62 |
| β-naphthoflavone | 15.40 ± 12.94 | 16.83 ± 0.96 | 6.52 ± 6.64 |
| Embelin | 13.54 ± 11.64 | 12.30 ± 10.24 | 5.95 ± 7.48 |
| trans-Cinnamic acid | 7.10 ± 6.95 | 4.66 ± 6.50 | 5.71 ± 10.53 |
| (−)-Epicatechin | 2.57 ± 11.60 | 15.02 ± 5.50 | 18.27 ± 9.34 |
| Phloridzin | 1.42 ± 9.28 | 3.76 ± 3.58 | 1.25 ± 7.90 |
| Puerarin | −12.86 ± 2.75 | −4.64 ± 3.47 | 0.43 ± 2.31 |
| Umbelliferone | −1081.56 ± 168.00 | −571.97 ± 117.56 | −280.41 ± 19.48 |

Figure 4A:
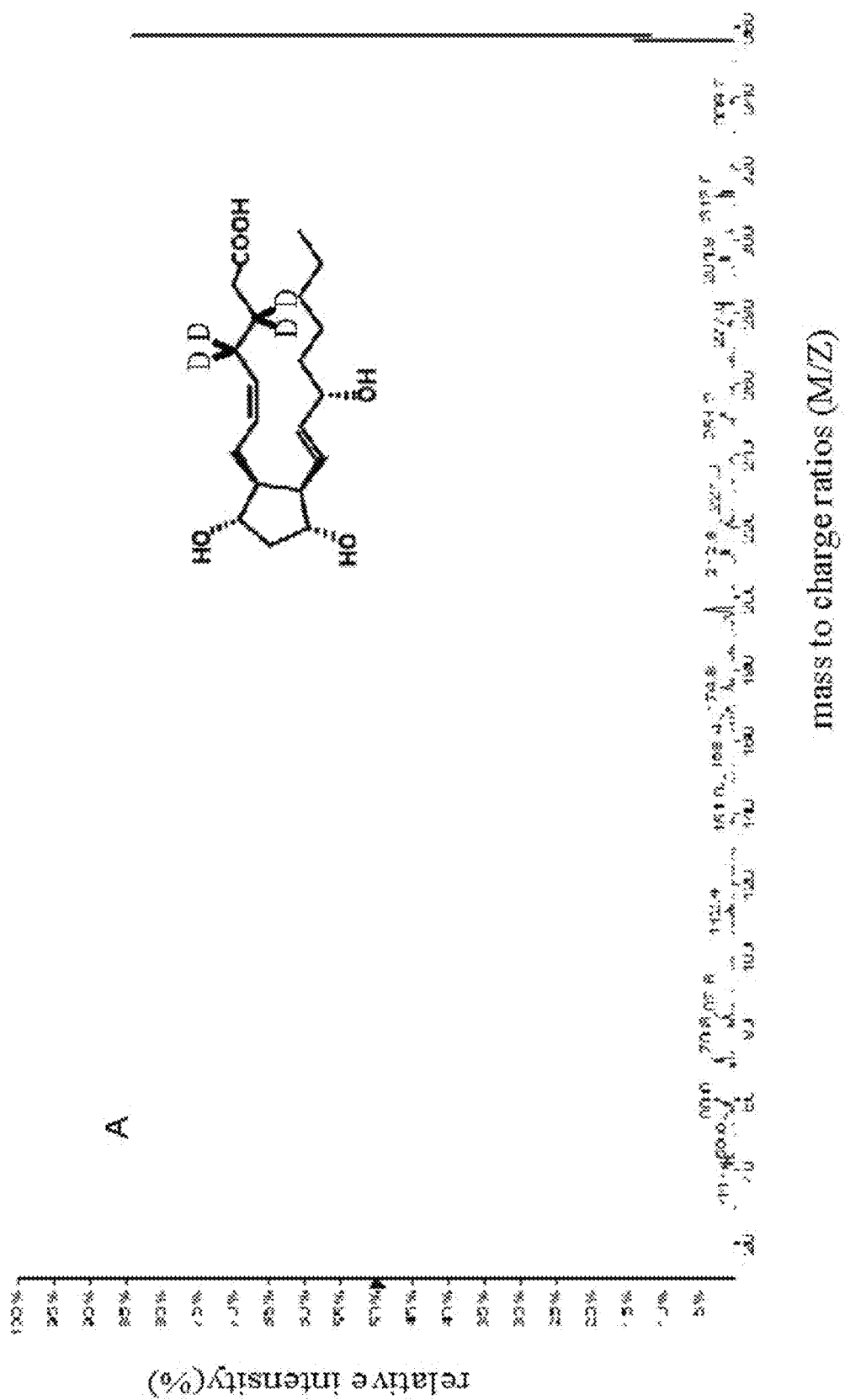
FIG. 4 shows the molecular structures and chronographs of 8-iso-PGF2α-d4 (A) and 8-iso-PGF2α (B).
Figure 4B:
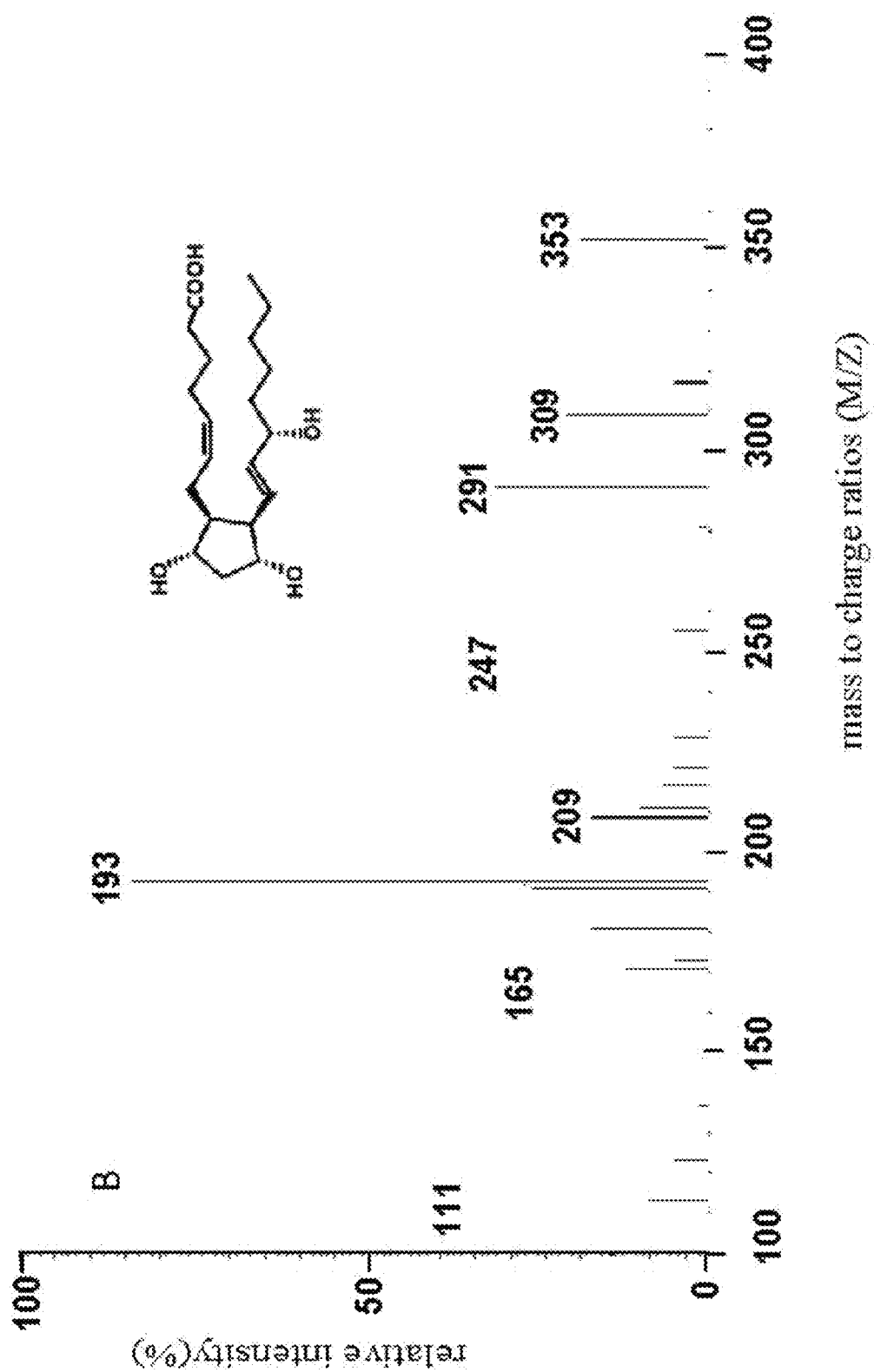
Figure 5:
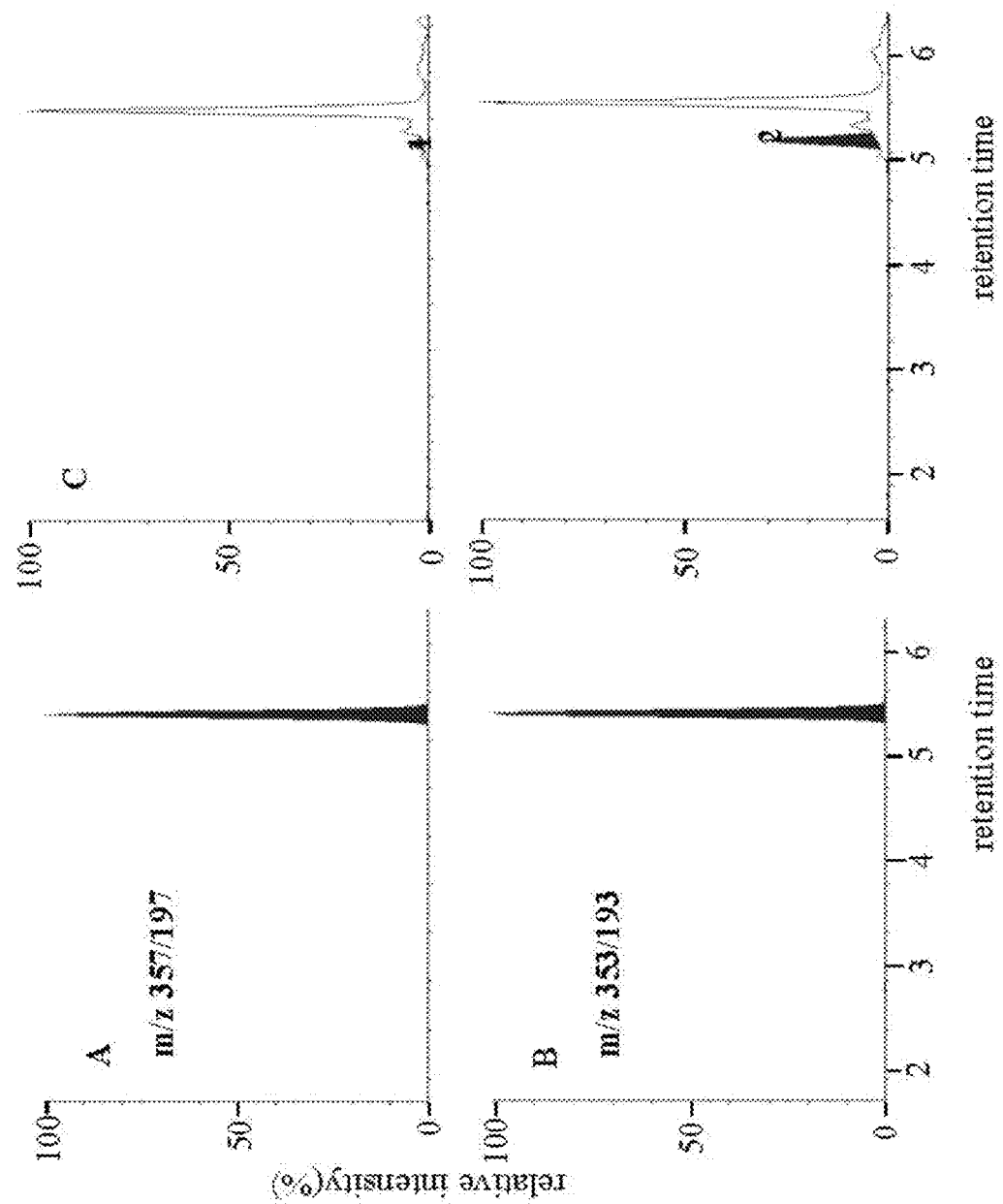
FIG. 5 shows LC/MS/MS chromatograph of reference compounds using MRM (multiple reaction monitor) mode. (A) Spiked with internal standard solution of 250 pg 8-iso-PGF2α-d4, (B) spiked with internal standard solution of 100 pg 8-iso-PGF2α, and (C) blank sample solution. Ion pairs are m/z 357/197 and m/z 353/193 for 8-iso-PGF2α-d4 (A) (as internal standard) and 8-iso-PGF2α(B) (as internal standard), respectively. Peak1: blank plasma; Peak 2: internal standard plasma.

The CYP 2E1 inhibition activity of various excipients was shown in FIG. 4. Different excipients have different inhibitory effects on cytochrome P450 under different conditions (0.167%, 0.08%, 0.042%, w/v) and among which 0.167% Brij 58 showed the best inhibition activity (97.75±0.66%).

TABLE 4

Inhibition of CYP 2E1 (%) by excipients

| Excipients | Inhibition of CYP2E1 (%) Tested concentration (w/v) | | |
|---|---|---|---|
| | 0.167% | 0.08% | 0.042% |
| Control | 0 | | |
| Positive control (DDTC) | 97.55 ± 1.862 | | |
| Brij 58 | 97.75 ± 0.66 | 96.58 ± 0.40 | 96.02 ± 0.17 |
| Brij 76 | 97.56 ± 1.02 | 96.87 ± 1.00 | 94.76 ± 0.47 |
| Brij 35 | 93.33 ± 0.82 | 89.45 ± 0.68 | 76.21 ± 7.37 |
| | (Tested concentration 0.025%) | (Tested concentration 0.013%) | (Tested concentration 0.006%) |
| Tween 20 | 87.20 ± 1.29 | 82.80 ± 1.71 | 71.77 ± 4.48 |
| Tween 80 | 73.92 ± 4.71 | 65.45 ± 2.50 | 64.02 ± 12.54 |
| Tween 40 | 58.97 ± 3.29 | 47.05 ± 6.48 | 44.79 ± 2.49 |
| PEG 2000 | 44.33 ± 2.75 | 40.13 ± 3.06 | 35.81 ± 3.26 |
| PEG 400 | 42.33 ± 5.25 | 39.10 ± 0.73 | 31.98 ± 5.97 |
| Pluornic F68 | 41.72 ± 5.34 | 42.98 ± 3.24 | 37.11 ± 10.35 |
| PEG 4000 | 37.21 ± 1.91 | 41.22 ± 0.97 | 37.18 ± 10.52 |

Example 3

Selection of Cytochrome P450 2E1 Inhibitors-Human Liver Microsomal Cytochrome P450 2E1

Materials and Methods
1. Materials

Microsomes prepared from human liver were used to extract cytochrome P450 2E1 (CYP2E1) and CYP2E1 inhibitors were screened from 39 Chinese herbal ingredients and 10 excipients. Chlorzoxazone hydroxylation is a reaction catalyzed primarily by CYP2E1 in liver. The extracted human liver microsomal cytochrome P450 2E1 (CYP2E1) was mixed with its substrate, Chlorzoxazone, and test sample was then added. Inhibition of CYP2E1 activity was calculated by measuring CYP2E1 standard metabolite, 6-OH-CZX (6-Hydroxy-Chlorzoxazone), and compared with control 6-OH-CZX.

All test samples were dissolved in 10% methanol or distilled water and guiding drugs and excipients at various concentrations were tested for their effects on inhibition of CYP2E1 activity. Tested Chinese herbal ingredients and excipients are shown in FIG. 3 and FIG. 4, respectively.

The materials required for screening human hepatocyte cytochrome P450 (CYP2E1) inhibitors are:
(1) CYP2E1: 100 mM potassium phosphate (pH 7.4) which contains 10 mg/ml P450 protein concentrate
(2) Control protein: 10 mg/ml P450 protein in 100 mM potassium phosphate (pH 7.4)
(3) Buffer solution: 0.5 M potassium phosphate (pH 7.4); stop solution: ice-acetonitrile
(4) Cofactors: include 100 mM NADP+ and 10 mM Glucose 6-Phosphate
(5) Glucose 6-Phosphate Dehydrogenase: 2000 units/ml in sterilized water
(6) Chlorzoxazone: substrate, 16 mM Chlorzoxazone in 10% methanol
(7) DDTC (Diethyldithiocarbamic acid): CYP2E1selective inhibitor (positive control), 20 mM DDTC in 10% methanol
(8) NADPH-regenerating System: add 530 μl Cofactor, 40 μl G6PDH (Glucose 6-Phosphate Dehydrogenase Solution) and 100 μl Control Protein to 3.42 ml 2. Screening of Cytochrome P450 2E1 (CYP2E1) Inhibitors
Experimental procedures for screening cytochrome P450 2E1 (CYP2E1) inhibitors:
(1) 0.1M potassium phosphate (pH 7.4) which contains 10 mg/ml P450 protein concentrate was mixed with 5 mM MgCl2 and incubated at 4° C. waterbath for 15 min,
(2) After incubation, 16 mM Chlorzoxazone and test samples were added toexperimental groups; methanol: sterilized water at 1:1 ratio was added to control groups and DDTC was added to positive control groups,
(3) Finally, cofactor 1 mM NADP+, 10 mM G6P and 2 IU G6PD were added and reaction mixtures were transferred to pre-incubation 37° C. water bath for 1 min and activity was measured after 30 min of reaction
(4) At the end of reaction, 500 μl acetonitrile was added to stop the reaction followed by 5 g/mL 4-hydroxy-tobutamide after 1 min incubation. The mixture was then centrifuged and 20 L of supernatant was diluted ten times with methanol/sterilized water and 5 L was used for LC/MS/MS analysis.
(5) Data analysis: the measured signal values obtained from LC/MS/MS analysis were logarithmically-transformed to give the amounts of CYP2E1 standard metabolite, 6-Hydroxy-Chlorzoxazone (pmol), using the control group as baseline with inhibition set at 0%. The inhibition of CYP2E1 was then calculated by the following equation:

$$\text{inhibition of } CYP2E1(\%) = 1 - \frac{\text{The amount of 6-OH-}CZX \text{ in experimental group}}{\text{Control 6-OH-}CZX}$$

Results
1. Positive Control

The inhibition of CYP 2E1 of positive control, DDTC, is shown in table 2 and according to table 2, DDTC can inhibit up to 87.56% of CYP 2E1 activity at concentration 100 μM.

TABLE 2

Inhibition of CYP 2E1 (%) by positive control

| DDTC concentration (μM) | 6-OH-CZX concentration (pmol) | CYP 2E1 inhibition (%) |
|---|---|---|
| 0 (control) | 3207.5 | 0 |
| 50 | 1644.5 | 48.66 |
| 100 | 431.2 | 87.56 |

2. The Experimental Groups

Inhibition of CYP 2E1 by Chinese herbal ingredients was shown in table 3 and suggested that different guiding drugs have different effects on cytochrome P450 CYP 2E1 activity at various concentrations (66 μM, 33 μM, 16.5 μM) and Nordihydroguaiaretic acid at 66 μM showed the best inhibition activity (96.98±0.19%).

TABLE 3

Inhibition of CYP 2E1 (%) by Chinese herbal ingredients

| Chinese herbal ingredients | Inhibition of CYP 2E1 (%) Tested Concentration | | |
|---|---|---|---|
| | 66 μM | 33 μM | 16.5 μM |
| Control | 0 | 0 | 0 |
| Nordihydroguaiaretic acid | 96.98 ± 0.19 | 67.68. ± 2.24 | 49.81 ± 2.42 |

TABLE 3-continued

Inhibition of CYP 2E1 (%) by Chinese herbal ingredients

| Chinese herbal ingredients | Inhibition of CYP 2E1 (%) Tested Concentration | | |
|---|---|---|---|
| | 66 μM | 33 μM | 16.5 μM |
| Trans-Cinnamaldehyde | 92.81 ± 0.53 | 89.56 ± 1.52 | 60.79 ± 3.00 |
| Daidzein | 86.77 ± 1.04 | 76.33 ± 2.28 | 73.55 ± 1.74 |
| Isovitexin | 81.82 ± 1.34 | 67.60 ± 3.24 | 59.82 ± 1.41 |
| Kaempferol | 79.25 ± 0.27 | 74.74 ± 0.60 | 66.53 ± 1.71 |
| Disulfiram | 78.23 ± 0.25 | 75.75 ± 1.38 | 74.09 ± 1.10 |
| β-Myrcene | 76.49 ± 2.18 | 75.50 ± 2.14 | 53.40 ± 4.93 |
| Quercetin | 73.32 ± 1.57 | 53.02 ± 2.17 | 46.40 ± 4.68 |
| (−)-Epigallocetechin-3-gallate | 72.16 ± 1.02 | 60.53 ± 2.06 | 50.19 ± 1.89 |
| (+)-Limonene | 63.64 ± 2.74 | 38.05 ± 1.95 | 13.77 ± 1.96 |
| Myricetin | 61.60 ± 0.88 | 59.21 ± 1.27 | 42.21 ± 2.55 |
| Quercitrin | 61.04 ± 5.88 | 53.77 ± 3.51 | 33.51 ± 4.29 |
| Luteolin-7-Glucoside | 60.26 ± 1.11 | 55.87 ± 0.67 | 42.96 ± 5.10 |
| Morin | 60.26 ± 1.56 | 52.08 ± 1.70 | 36.88 ± 1.56 |
| Neohesperidin | 58.70 ± 1.06 | 48.96 ± 2.37 | 42.81 ± 1.75 |
| Hesperidin | 58.57 ± 3.78 | 50.91 ± 2.81 | 45.32 ± 1.57 |
| Capillarisin | 57.31 ± 1.31 | 46.22 ± 2.65 | 32.89 ± 2.46 |
| (−)-Epigallocatechin | 57.08 ± 1.85 | 36.40 ± 2.18 | 38.95 ± 1.92 |
| Hyperoside | 53.51 ± 1.20 | 35.58 ± 3.68 | −24.16 ± 1.19 |
| Luteolin | 53.23 ± 1.78 | 43.40 ± 4.74 | 39.15 ± 3.42 |
| Ethyl Myristate | 51.95 ± 2.38 | 41.04 ± 4.76 | 22.08 ± 0.78 |
| Tamarixetin | 50.91 ± 3.12 | 47.79 ± 2.81 | 37.40 ± 1.96 |
| Phloretin | 50.90 ± 2.09 | 39.78 ± 3.28 | 29.60 ± 3.21 |
| Baicalein | 50.13 ± 5.11 | 47.79 ± 3.40 | 35.32 ± 1.51 |
| Baicalin | 49.30 ± 2.26 | 35.61 ± 3.09 | 22.51 ± 2.24 |
| Apigenin | 47.51 ± 3.66 | 36.80 ± 1.98 | 28.89 ± 1.54 |
| Naringenin | 45.16 ± 4.43 | 28.45 ± 2.21 | 19.50 ± 2.02 |
| Hesperetin | 44.56 ± 2.35 | 34.28 ± 2.03 | 25.74 ± 2.45 |
| (+)-Epicatechin | 44.32 ± 1.25 | 52.32 ± 1.59 | 66.71 ± 1.79 |
| Rutin | 43.51 ± 3.09 | 30.13 ± 1.62 | 30.00 ± 0.81 |
| (−)-Epicatechin-3-gallate | 42.92 ± 0.65 | 34.84 ± 1.72 | 30.31 ± 1.27 |
| Isoliquritigenin | 41.12 ± 0.92 | 31.48 ± 1.24 | 21.18 ± 1.96 |
| Silybin | 38.96 ± 1.19 | 37.14 ± 1.15 | 59.48 ± 2.34 |
| Vitexin | 38.70 ± 1.62 | 30.65 ± 0.78 | 23.12 ± 1.19 |
| Genistein | 36.88 ± 1.56 | 30.91 ± 1.62 | 43.90 ± 2.06 |
| Isorhamnetin | 36.31 ± 1.59 | 18.68 ± 1.22 | 12.06 ± 1.06 |
| gallic acid | 27.96 ± 1.56 | 18.79 ± 2.03 | 10.50 ± 1.12 |
| Diosmin | 21.56 ± 1.19 | 43.12 ± 3.57 | 60.00 ± 1.96 |
| 6-Gingerol | 19.08 ± 1.36 | 11.51 ± 1.02 | 7.84 ± 0.92 |

CYP 2E1 inhibition by excipients was shown in table 4 and indicated that different excipients have different effects on cytochrome P450 CYP 2E1 activity at various concentrations (0.167%, 0.08%, 0.042%, w/v) and 0.167% Brij 58 has the best inhibition of 91.24±1.33%.

TABLE 4

Inhibition of CYP 2E1 (%) by excipients

| Excipients | Inhibition of CYP 2E1 (%) Tested concentration (w/v) | | |
|---|---|---|---|
| | 0.167% | 0.08% | 0.042% |
| Control | 0 | 0 | 0 |
| Brij 58 | 91.24 ± 1.33 | 80.50 ± 1.14 | 62.57 ± 2.10 |
| Brij 76 | 86.15 ± 1.02 | 75.71 ± 1.61 | 68.99 ± 3.77 |
| Brij 35 | 77.28 ± 1.02 | 64.17 ± 1.71 | 42.37 ± 1.78 |
| | (Tested concentration 0.025%) | (Tested concentration 0.013%) | (Tested concentration 0.006%) |
| Tween 20 | 75.38 ± 3.64 | 70.44 ± 0.93 | 55.38 ± 1.95 |
| PEG 400 | 64.17 ± 1.53 | 54.78 ± 3.53 | 26.42 ± 1.81 |
| PEG 4000 | 47.11 ± 0.92 | 23.94 ± 0.92 | 8.70 ± 0.77 |
| PEG 2000 | 47.06 ± 1.53 | 41.43 ± 1.60 | 22.25 ± 1.93 |
| Tween 40 | 46.34 ± 3.06 | 33.43 ± 2.10 | 16.88 ± 1.17 |
| Tween 80 | 39.14 ± 2.40 | 40.56 ± 3.85 | 29.02 ± 1.67 |
| Pluornic F68 | 31.46 ± 1.60 | 17.39 ± 1.07 | 7.93 ± 0.27 |

Compare to the test results from isoniazid treatment alone, e.g. biochemical analysis (ALT and AST values); pathology results; residual liver function tests (GSP and GEC values), and indicator of oxidative stress (serum concentration of 8-iso-PGF2α) etc., the novel and low side-effect isoniazid (INH) pharmaceutical composition claimed in the present invention can significantly reduce INH-induced hepatotoxicity.

The detailed description mentioned above was to better elucidate the present invention, and it should be understood that the applications of the present invention is not limited to the description provided here, e.g. the concentrations and ratios of isoniazid ((INH), Cytochrome P450 2E1 inhibitors, disulfuram (DSF), and bis-nitrophenyl phosphate (BNPP) or the combinations of various Cytochrome P450 inhibitors etc. and all related applications should be included in the present invention.

What is claimed is:

1. A low side-effect pharmaceutical composition containing isoniazid, comprising a pharmaceutically effective amount of isoniazid and a cytochrome P450 2E1 inhibitor.

2. The pharmaceutical composition according to claim 1, wherein the cytochrome p450 2E1 inhibitor is disulfuram (DSF).

3. The pharmaceutical composition according to claim 1, wherein the cytochrome p450 2E1 inhibitor was selected from the following compounds: Nordihydroguaiaretic acid, Trans-Cinnamaldehyde, Daidzein, isovitexin, Kaempferol, disulfuram, β-Myrcene, Quercetin, (−)-Epigallocatechin-3-gallate, Morin, (+)-Limonene, Myricetin, Quercitrin, Luteolin-7-Glucoside, Neohesperidin, Hesperidin, Capillarisin, (−)-Epigallocatechin, Luteolin, Hyperoside, Ethyl Myristate, Tamarixetin, Phloretin, Tamarixetin, Baicalein, Rutin, Baicalin, Apigenin, Naringenin, Hesperetin, (+)-Epicatechin, Isoliquritigenin, (−)-Epicatechin-3-gallate, Silybin, Vitexin, Isorhamnetin, gallic acid, Diosmin, 6-Gingerol, (+)-Taxifolin, Wongonin, Protocatechuic acid, (+)-Catechin, β-naphthoflavone, Embelin, Trans-Cinnamic acid, (−)-Epicatechin, Phloridzin, Puerarin, Umbelliferone Brij 58, Brij 76, Brij 35, Tween 20, Tween 80, Tween 40, PEG 2000, PEG 400, Pluornic F68 and PEG 4000.

4. The pharmaceutical composition according to claim 1, further comprising suitable pharmaceutical acceptable excipients.

5. The pharmaceutical composition according to claim 4, wherein the excipients are diluents, fillers, binders, disintegrants or lubricants.

6. A low side-effect pharmaceutical composition containing isoniazid, comprising a pharmaceutically effective amount of isoniazid, disulfuram and bis-p-nitrophenylphosphate.

7. The pharmaceutical composition according to claim 6, wherein the composition includes suitable pharmaceutical acceptable excipients.

8. The pharmaceutical composition according to claim 6, wherein the excipients are diluents, fillers, binders, disintegrants or lubricants.

* * * * *